United States Patent [19]
Tanoue et al.

[11] Patent Number: 5,886,011
[45] Date of Patent: Mar. 23, 1999

[54] PIPERIDINE DERIVATIVES AS SUBSTANCE P ANTAGONISTS

[75] Inventors: Yoshihiro Tanoue; Koichi Beppu; Akira Okayama; Osami Sakamoto, all of Tosu, Japan

[73] Assignee: Hisamitsu Pharmaceutical Co., Inc., Saga, Japan

[21] Appl. No.: 913,824

[22] PCT Filed: Mar. 27, 1996

[86] PCT No.: PCT/JP96/00796

§ 371 Date: Sep. 26, 1997

§ 102(e) Date: Sep. 26, 1997

[87] PCT Pub. No.: WO96/30367

PCT Pub. Date: Mar. 10, 1996

[30] Foreign Application Priority Data

Mar. 27, 1995 [JP] Japan ................................. 7-093150

[51] Int. Cl.⁶ ..................... A61K 31/445; C07D 405/12; C07D 307/79
[52] U.S. Cl. ..................... 514/320; 514/321; 546/196; 546/197
[58] Field of Search ..................... 546/196, 197; 514/320, 321

[56] References Cited

U.S. PATENT DOCUMENTS 5,393,762  2/1995  Desai et al. ............................ 514/331

FOREIGN PATENT DOCUMENTS

WO 9413663  6/1994  WIPO .

OTHER PUBLICATIONS

Mishina et al. "Preparation of imidazolybenzene compounds and use thereof as medicines" CA 123:83361, 1995.
Naylor et al. "Preparation of benzofuran derivatives as tachykinin antagonists" CA 123:339709, 1995.

*Primary Examiner*—Ceila Chang
*Attorney, Agent, or Firm*—Townsend & Banta

[57] ABSTRACT

Piperidine derivatives represented by general formula (I)

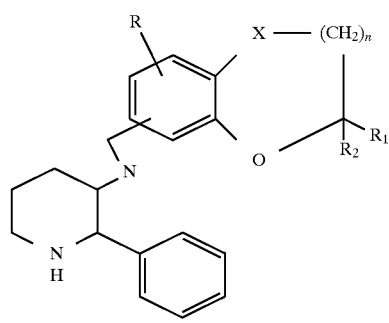

or pharmaceutically acceptable acid addition salts thereof: wherein n represents an integer of 0 or 1; X represents $CH_2$, O or $CH-CH_3$; R represents hydrogen, halogen, lower alkyl, hydroxy, lower alkoxy, lower alkylthio, lower alkylsulfinyl, lower alkylsulfonyl, substituted aminosulfonyl or nitro; $R_1$ and $R_2$ may be the same or different and each represents hydrogen or lower alkyl, are disclosed. The piperidine derivatives have an antagonism on Substance P and is useful as a preventive or remedy for asthma, vomiting, etc.

15 Claims, No Drawings

PIPERIDINE DERIVATIVES AS SUBSTANCE P ANTAGONISTS

This application is a 371 of PCT/JP96/00796 filed Mar. 27, 1996.

TECHNICAL FIELD

The present invention relates to new piperidine derivatives having an antagonism on Substance P, being a peptide neurotransmitter, and pharmaceutically acceptable acid addition salts thereof. The piperidine derivatives and pharmaceutically acceptable acid addition salts thereof of the present invention are useful as a preventive or remedy for respiratory system diseases, central nervous system diseases, digestive system diseases, circulatory system diseases, and a variety of inflammation and pains and the like.

PRIOR ART

Substance P is a tachykinin undecapeptide which is found especially in mammals and which is referred as Neurokinin with Neurokinin A and Neurokinin B etc. The facts that Substance P is involved in a variety of pathological fields such as respiratory system diseases such as asthma, central nervous system diseases such as anxiety, schizophrenia, digestive system diseases such as ulcerative colitis, circulatory system diseases such as hypertension, various inflammation and pains, have been well-known (e.g., Journal of Medicinal Chemistry,25,1009, (1982), Trends in Cluster Headache, 85–97, (1987),ELSEVIER).

In addition, until now, as the non-peptide Substance P antagonist, a compound having a quinuclidine skeleton (JP 3-503768, A), a compound having a piperidine skeleton (JP 4-103570, A), a compound having an isoindolone skeleton (JP 3-176469, A), a compound having an arylalkylamine skeleton (JP 3-206086, A) etc. have been known.

As the compounds having benzofuran ring or benzopyran ring, the compound described in WO93/09116 has been known. The non-aromatic alicyclic compound substituted by an aminomethylene group is disclosed in WO94/13663. A remedy for vomiting is disclosed in JP 7-53362, A. The compounds of the present invention are included in the compounds described in WO94/13663 and JP 7-53362, as subordinate concepts. However, the compounds of the present invention as well as the similar compounds are not disclosed in any publications concretely.

DISCLOSURE OF THE INVENTION

The object of the present invention is to provide piperidine derivatives or pharmaceutically acceptable acid addition salts thereof having an antagonism on non-peptide Substance P.

The present invention provides piperidine derivatives represented by general formula (I)

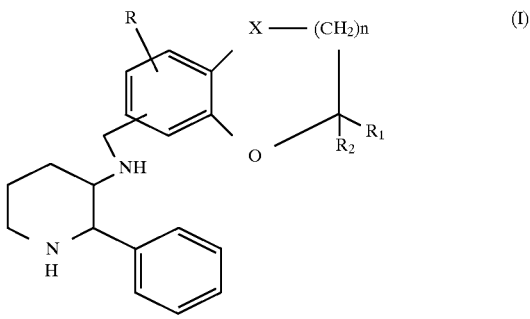

or pharmaceutically acceptable acid addition salts thereof: wherein n represents an integer of 0 or 1; X represents $CH_2$, O or CH—$CH_3$; R represents hydrogen, halogen, lower alkyl, hydroxy, lower alkoxy, lower alkylthio, lower alkylsulfinyl, lower alkylsulfonyl, substituted aminosulfonyl or nitro; $R_1$ and $R_2$ may be the same or different and each represents hydrogen or lower alkyl.

The present invention also provides cis-piperidine derivatives represented by general formula (Ia)

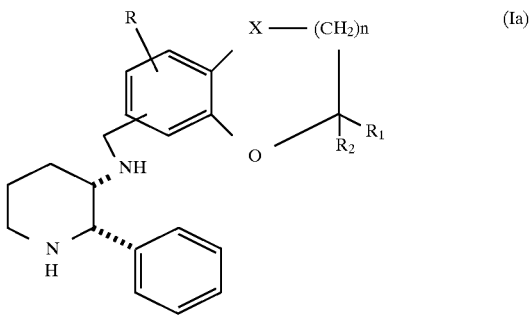

or pharmaceutically acceptable acid addition salts thereof: wherein n, X, R, $R_1$ and $R_2$ are as defined above.

The present invention also provides cis-piperidine derivatives represented by general formula (Ib)

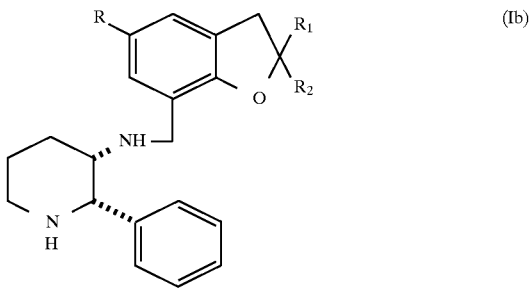

or pharmaceutically acceptable acid addition salts thereof: wherein R, $R_1$ and $R_2$ are as defined above.

The present invention also provides the piperidine derivatives or pharmaceutically acceptable acid addition salts thereof having an antagonism on Substance P.

The present invention also provides a pharmaceutical composition comprising an effective amount of the piperidine derivative or pharmaceutically acceptable acid addition salt thereof, and a pharmaceutically acceptable carrier.

The present invention also provides a preventive or remedy for asthma which comprises the piperidine derivative or pharmaceutically acceptable acid addition salt thereof as an effective component.

The present invention also provides a preventive or remedy for vomiting which comprises the piperidine derivative or pharmaceutically acceptable acid addition salt thereof as an effective component.

The present invention also provides a formulation for oral administration, a formulation for parenteral administration, a formulation for intrarectal administration or a formulation for percutaneous administration which comprises the piperidine derivative or pharmaceutically acceptable acid addition salt thereof as an effective component.

The present invention will be explained, hereinafter.

The compounds represented by the general formula (I), (Ia) and (Ib) of the present invention will be explained concretely.

In the above general formulas (I), (Ia) and (Ib), n represents an integer of 0 or 1. When n is 0, a form of condensed five-membered ring with benzen ring is shown. When n is 1, a form of condensed six-membered ring with benzen ring is shown.

X represents $CH_2$, O or $CH—CH_3$ substituted by a methyl group from methylene group in the ring.

In the formulas, R represents a substituent group on the phenyl group in the condensed ring, including non-substituted condition. R represents hydrogen, halogen, lower alkyl, hydroxy, lower alkoxy, lower alkylthio, lower alkylsulfinyl, lower alkylsulfonyl, substituted aminosulfonyl or nitro.

In the specification, halogen means fluorine, chlorine, bromine or iodine.

The lower alkyl group represents a cyclic or acyclic alkyl group having $C_{1-6}$ which may contain one to five halogen such as fluorine in any position. As the lower alkyl group, methyl, ethyl, n-propyl, iso-propyl, n-butyl, iso-butyl, tert-butyl, n-pentyl, n-hexyl, cyclopentyl, cyclohexyl, monofluoromethyl, difluoromethyl, trifluoromethyl, trifluoro-ethyl and perfluoroethyl may be exemplified.

The lower alkoxy group represents a cyclic or acyclic alkoxy group having $C_{1-6}$ which may contain one to five halogen such as fluorine in any position. As the lower alkoxy group, methoxy, ethoxy, n-propoxy, iso-propoxy, n-butoxy, iso-butoxy, tert-butoxy, n-pentyloxy, n-hexyloxy, cyclopentyloxy, cyclohexyloxy, monofluoromethoxy, difluoromethoxy, trifluoromethoxy, trifluoroethoxy and perfluoroetyoxy may be exemplified.

The lower alkylthio group represents a cyclic or acyclic alkylthio group having $C_{1-6}$ which may contain one to five halogen atoms such as fluorine in any position. As the lower alkylthio group, methylthio, ethylthio, n-propylthio, iso-propylthio, n-butylthio, iso-butylthio, tert-butylthio, n-pentylthio, n-hexylthio, cyclopentylthio, cyclohexylthio, monofluoromethylthio, difluoromethylthio, trifluoromethylthio, trifluoroethylthio, perfluoroethylthio may be exemplified.

As the lower alkylsulfinyl group represents a cyclic or acyclic alkylsulfinyl group having $C_{1-6}$ which may contain one to five halogen atoms such as fluorine in any position. As the lower alkylsulfinyl group, methylsulfinyl, ethylsulfinyl, n-propylsulfinyl, iso-propylsulfinyl, n-butylsulfinyl, iso-butylsulfinyl, tert-butylsulfinyl, n-pentylsulfinyl, n-hexylsulfinyl, cyclopentylsulfinyl, cyclohexylsulfonyl, monofluoromethylsulfinyl, difluoromethylsulfinyl, trifluoromethylsulfinyl, trifluoroethylsulfinyl, perfluoroethylsulfinyl may be exemplified.

The lower alkylsulfonyl group represents a cyclic or acyclic alkylsulfonyl group having $C_{1-6}$ which may contain one to five halogen atoms such as fluorine in any position. As the lower alkylsulfonyl group, methylsulfonyl, ethylsulfonyl, n-propylsulfonyl, iso-propylsulfonyl, n-butylsulfonyl, iso-butylsulfonyl, tert-butylsulfonyl, n-pentylsulfonyl, n-hexylsulfonyl, cyclopentylsulfonyl, cyclohexylsulfonyl, monofluoromethylsulfonyl, difluoromethylsulfonyl, trifluoro-methylsulfonyl, trifluoroethylsulfonyl, perfluoroethyl-sulfornyl may be exemplified.

The substituted aminosulfonyl group represents a cyclic or acyclic alkylaminosulfonyl group having $C_{1-6}$ which may contain one to five halogen atoms such as fluorine in any position, and represents an aminosulfonyl group in which an amino group forms a part of the cyclic compound. As the substituted aminosulfonyl group, methylaminosulfonyl, ethylaminosulfonyl, n-propylaminosulfonyl, iso-propylaminosulfonyl, n-butylaminosulfonyl, iso-butylaminosulfonyl, tert-butylaminosulfonyl, n-pentylaminosulfonyl, n-hexylaminosulfonyl, dimethylaminosulfonyl, diethylaminosulfonyl, di-n-propylaminosulfonyl, diisopropylaminosulfonyl, di-n-butylaminosulfonyl, diisobutylaminosulfonyl, cyclopentylaminosulfonyl, cyclohexylaminosulfonyl, monofluoromethylaminosulfonyl, difluoromethylaminosulfonyl, trifluoromethylaminosulfonyl, trifluoroethylaminosulfonyl, perfluoroethylaminosulfonyl, 1-pyrrolidinylsulfonyl, 1-piperidinylsulfonyl, 1-dihydropyrrolidinylsulfonyl, 1-dihydropyridinylsulfonyl may be exemplified.

$R_1$ and $R_2$ may be the same or different and each represents hydrogen or a lower alkyl. As the lower alkyl group, methyl, ethyl, n-propyl, isopropyl, n-butyl, isobutyl may be exemplified. Depending on the combination of $R_1$ and $R_2$, the forms of unsubstitution, monoalkyl and dialkyl may be made.

The present invention includes any forms of stereoisomers produced in monoalkyl, diastereomer and mixtures thereof. In addition, the present invention includes both of cis-isomer and trans-isomer of the compound (I), among which cis-isomer represented by the formula (Ia) is most preferable.

As examples of the pharmaceutically acceptable acid addition salts, salts formed with an inorganic acid such as hydrochloric acid, hydrobromic acid, sulfuric acid, nitric acid, phosphoric acid: or salts formed with an organic acid such as acetic acid, propionic acid, glycolic acid, lactic acid, malic acid, tartaric acid, citric acid, ascorbic acid, maleic acid, oxalic acid, fumaric acid, succinic acid, malonic acid, methanesulfonic acid, benzensulfonic acid, toluene-sulfonic acid, may be exemplified. The acid addition salts are, however, not limited by the examples.

As preferable examples of the compounds represented by the general formula (I) and the acid addition salts thereof, (2S,3S)-3-[(2,2-dimethyl-2,3-dihydrobenzofuran-7-yl) methyl]amino-2-phenylpiperidine hydrochloride, (2S,3S)-3-[(2-methyl-2,3-dihydrobenzofuran-7-yl) methyl]amino-2-phenylpiperidine hydrochloride, (2S,3S)-3-[(2,2-dimethyl-5-nitro-2,3-dihydrobenzofuran-7-yl)methyl]amino-2-phenylpiperidine hydrochloride, (2S,3S)-3-[(2,2-dimethyl-5-methylthio-2,3-dihydrobenzofuran-7-yl)methyl]amino-2-phenylpiperidine hydrochloride, (2S,3S)-3-[(2,2-dimethyl-5-methylsulfonyl-2,3-dihydrobenzofuran-7-yl)methyl]amino-2-phenylpiperidine hydrochloride, (2S,3S)-3-[(2,2-dimethyl-5-dimethylaminosulfonyl-2,3-dihydrobenzofuran-7-yl)methyl]amino-2-phenylpiperidine hydrochloride, (2S,3S)-3-[(5-dimethylaminosulfonyl-2-methyl-2,3-dihydrobenzofuran-7-yl)methyl]amino-2-phenylpiperidine hydrochloride, (2S,3S)-3-(3,4-methylenedioxybenzyl)amino-2-phenyl-piperidine hydrochloride, (2S,3S)-3-[(3,4-dihydro-1,2-benzopyran-8-yl)methyl]amino-2-phenylpiperidine hydrochloride, (2S,3S)-3-[(5-chloro-2,2-dimethyl-2,3-dihydrobenzofuran-7-yl)methyl]amino-2-phenylpiperidine hydrochloride, (2S,3S)-3-[(2,2-dimethyl-5-methoxy-2,3-dihydrobenzofuran-7-yl)methyl]amino-2-phenylpiperidine hydrochloride, (2S,3S)-3-[(2,3-dihydrobenzofuran-7-yl)methyl]amino-2-phenylpiperidine hydrochloride, (2S,3S)-3-[(5-chloro-2-methyl-2,3-dihydrobenzofuran-7-yl)methyl]amino-2-phenylpiperidine hydrochloride, (2S,3S)-3-[(5-methoxy-2-methyl-2,3-dihydrobenzofuran-7-yl)methyl]amino-2-phenylpiperidine hydrochloride, (2S,3S)-3-[(2,2,4-trimethyl-2,3-dihydrobenzofuran-7-yl)methyl]amino-2-phenylpiperidine hydrochloride, (2S,3S)-3-[(2,2,5-trimethyl-2,3-dihydrobenzofuran-7-yl)methyl]amino-2-phenylpiperidine hydrochloride, (2S,3S)-3-[(4-chloro-2,2-dimethyl-2,3-dihydrobenzofuran-7-yl)methyl]amino-2-phenylpiperidine hydrochloride, (2S,3S)-3-(3,4-methylenedioxybenzyl)amino-2-phenylpiperidine hydrochloride, (2S,3S)-3-[(2,3-dimethyl-2,3-dihydrobenzofuran-7-yl)methyl]amino-2-phenylpiperidine hydrochloride, (2S,3S)-3-[(2,3,4-trimethyl-2,3-dihydrobenzofuran-7-yl)methyl]amino-2-phenylpiperidine hydrochloride, (2S,3S)-3-[(2,5-dimethyl-2,3-dihydrobenzofuran-7-yl)methyl]amino-2-phenylpiperidine hydrochloride, (2S,3S)-3-[(5-isopropyl-2,3-dihydrobenzofuran-7-yl)methyl]amino-2-phenylpiperidine hydrochloride, (2S,3S)-3-[(5-tert.butyl-2,3-dihydrobenzofuran-7-yl)methyl]amino-2-phenylpiperidine hydrochloride, (2S,3S)-3-[(5-cyclopentyl-2,3-dihydrobenzofuran-7-yl)methyl]amino-2-phenylpiperidine hydrochloride, (2S,3S)-3-[(5-cyclohexyl-2,3-dihydrobenzofuran-7-yl)methyl]amino-2-phenylpiperidine hydrochloride, (2S,3S)-3-[(5-ethylthio-2,3-dihydrobenzofuran-7-yl)methyl]amino-2-phenylpiperidine hydrochloride, (2S,3S)-3-[(5-isopropylthio-2,3-dihydrobenzofuran-7-yl)methyl]amino-2-phenylpiperidine hydrochloride, (2S,3S)-3-[(5-cyclohexylthio-2,3-dihydrobenzofuran-7-yl)methyl]amino-2-phenylpiperidine hydrochloride, (2S,3S)-3-[(5-trifluoromethylthio-2,3-dihydrobenzofuran-7-yl)methyl]amino-2-phenylpiperidine hydrochloride, (2S,3S)-3-[(5-(2,2,2-trifluoro)ethylthio-2,3-dihydrobenzofuran-7-yl)methyl]amino-2-phenylpiperidine hydrochloride, (2S,3S)-3-[(5-methylsulfinyl-2,3-dihydrobenzofuran-7-yl)methyl]amino-2-phenylpiperidine hydrochloride, (2S,3S)-3-[(5-isopropylsulfonyl-2,3-dihydrobenzofuran-7-yl)methyl]amino-2-phenylpiperidine hydrochloride, (2S,3S)-3-[(5-isopropylsulfonyl-2-methyl-2,3-dihydrobenzofuran-7-yl)methyl]amino-2-phenylpiperidine hydrochloride, (2S,3S)-3-[(5-cyclopentylsulfonyl-2,3-dihydrobenzofuran-7-yl)methyl]amino-2-phenylpiperidine hydrochloride, (2S,3S)-3-[(2-methyl-5-methylaminosulfonyl-2,3-dihydrobenzofuran-7-yl)methyl]amino-2-phenylpiperidine hydrochloride, (2S,3S)-3-[(5-methoxy-2,3-dihydrobenzofuran-7-yl)methyl]amino-2-phenylpiperidine hydrochloride, (2S,3S)-3-[(2,2-dimethyl-5-fluoro-2,3-dihydrobenzofuran-7-yl)methyl]amino-2-phenylpiperidine hydrochloride, (2S,3S)-3-[(5-hydroxy-2-methyl-2,3-dihydrobenzofuran-7-yl)methyl]amino-2-phenylpiperidine hydrochloride, (2S,3S)-3-[(5-fluoro-2-methyl-2,3-dihydrobenzofuran-7-yl)methyl]amino-2-phenylpiperidine hydrochloride, (2S,3S)-3-[(5-nitro-2,3-dihydrobenzofuran-7-yl)methyl]amino-2-phenylpiperidine hydrochloride, (2S,3S)-3-[(2-methyl-5-methylsulfonyl-2,3-dihydrobenzofuran-7-yl)methyl]amino-2-phenylpiperidine hydrochloride, (2S,3S)-3-[(2-methyl-5-methylthio-2,3-dihydrobenzofuran-7-yl)methyl]amino-2-phenylpiperidine hydrochloride, (2S,3S)-3-[(5-dimethylaminosulfonyl-2,3-dihydrobenzofuran-7-yl)methyl]amino-2-phenylpiperidine hydrochloride, (2S,3S)-3-[(5-methylsulfonyl-2,3-dihydrobenzofuran-7-yl)methyl]amino-2-phenylpiperidine hydrochloride, (2S,3S)-3-[(5-methylthio-2,3-dihydrobenzofuran-7-yl)methyl]amino-2-phenylpiperidine hydrochloride, (2S,3S)-3-[(5-methyl-2,3-dihydrobenzofuran-7-yl)methyl]amino-2-phenylpiperidine hydrochloride, (2S,3S)-3-[(5-chloro-2,3-dihydrobenzofuran-7-yl)methyl]amino-2-phenylpiperidine hydrochloride, (2S,3S)-3-[(5-ethoxy-2-methyl-2,3-dihydrobenzofuran-7-yl)methyl]amino-2-phenylpiperidine hydrochloride, (2S,3S)-3-[(5-cyclopentyloxy-2-methyl-2,3-dihydrobenzofuran-7-yl)methyl]amino-2-phenylpiperidine hydrochloride, (2S,3S)-3-[(2,4-dimethyl-5-dimethylaminosulfonyl-2,3-dihydrobenzofuran-7-yl)methyl]amino-2-phenylpiperidine hydrochloride, (2S,3S)-3-[(2-methyl-5-(1-pyrrolidinyl)sulfonyl-amino-2,3-dihydrobenzofuran-7-yl)methyl]amino-2-phenylpiperidine hydrochloride, and (2S,3S)-3-[(5-trifluoromethoxy-2,3-dihydrobenzofuran-7-yl)methyl]amino-2-phenylpiperidine hydrochloride, may be exemplified.

The piperidine derivatives and pharmaceutically acceptable acid addition salts thereof of the present invention are useful as a preventive or remedy for respiratory system diseases, central nervous system diseases, digestive system diseases, circulatory system diseases, and a variety of inflammation and pains and the like. As concrete examples of these diseases and inflammations, chronic bronchial obstruction, asthma, migraine, vomiting, anxiety, depression, melancholia, Alzheimer's diseases, dementia, stomatosis caused by stress, anaphylaxis, colitis, hypertension, vasospamic diseases, hidebound disease, arthritis, psoriasis, rheumatic diseases, multiple sclerosis, systemic lupus erythematosus, initis, drug toxicosis may be exemplified.

When the compound represented by the general formula (I), (Ia) or (Ib) or the pharmaceutically acceptable acid addition salt thereof is administered as a drug, it may be administered as it is, or it may be made into any forms of formulations for oral administration, parenteral administration, intrarectal administration and percutaneous administration together with known carriers.

The formulation for oral administration is not limited to, but solid or liquid formulations such as powdered drug, powders, capsules, granules, tablets, syrups, elixirs or suspensions may be exemplified.

The powdered drug can be prepared by powdering the effective component into an appropriate particle size. The powders can be prepared by powdering the effective component into an appropriate particle size, and then mixing with a pharmaceutically acceptable carrier which has been powdered similarly, such as carbohydrates such as starch and mannitol and another excipients. The powdered drug and the powders may contain, if necessary, flavoring agents, preservatives, dispersers, colorants, aromas, etc.

The capsules can be prepared by filling the above powdered-drug, powders or granules into the external skin of a capsule such as gelatin capsule. Before filling, the powdered-drug, powders, granules may be mixed with lubricants, fluidizing agents e.g., colloidal silica, talc, magnesium stearate, calcium stearate, solid polyethylene glycol etc. In addition, disintegrants and plasticizers such as carboxymethyl cellulose, calcium carboxymethyl cellulose, hydroxypropyl cellulose having a lower degree of substitution, sodium croscarmellose, sodium carboxystarch, calcium carbonate, sodium carbonate and the like, may be added to them.

The granules can be prepared by mixing the powdered effective component and the above excipients and disintegrants, and adding binders (e.g., sodium carboxymethyl cellulose, hydroxypropylcellulose, methylcellulose, hydroxy propylmethylcellulose, gelatin, polyvinyl pyrrolidone, polyvinyl alcohol) and humectants (e.g., syrups, starch glue, gum arabic, cellulose solution or high-molecule material solutions) to them and kneading, and then force-passing them through sieves. Alternatively, instead of granulating powders in such a way, after treating powders with a tablet press, the obtained incomplete forms of slugs may be powdered to obtain granules. Solution retarder (e.g., paraffin, wax, hardened castor oil), reabsorbent (e.g., quaternary salts) or adsorbent (e.g., bentonite, kaolin, dicalcium phosphate) may be mixed in previously.

The tablets may be prepared by adding stearic acid, stearate, talc, mineral oils as tablet lubricant to the granules thus obtained, and tabletting. In addition, coating of a high-molecular material such as sugar, transparent or semi-transparent protective coating comprising sealed coating of shellac, polishing coating comprising wax and the like may be provided on the obtained uncoated-tablet. The effective component may be tabletted directly after mixing with fluid inactive carriers, without steps such as the granulating or the slugging.

The syrups may be prepared by dissolving effective component in an appropriate flavored aqueous solution. The elixirs may be prepared by dissolving effective component in a non-toxic alcohol carrier. The suspensions may be prepared by dissolving effective component in a non-toxic carrier. To the syrups, elixirs and suspensions, suspending agents, emulsifying agents (e.g., ethoxylated isostearyl alcohols, polyoxyethylene sorbitol esters), preservatives, flavoring agent (e.g., peppermint oil, saccharin) and the like may be added if desired.

The formulation for parenteral administration includes formulations for subcutaneous, intramuscular, intraarterial and intravenous administrations. The formulation for parenteral administration may be formed into solutions and suspensions. The formulation for parenteral administration may be prepared by dissolving or suspending a determined amount of the effective component into a non-toxic liquid carrier suitable for the purpose of the injection such as aqueous or oily solutions, and then sterilizing the solution or suspension. Alternatively, the formulation for parenteral administration may be prepared by filling a determined amount of the powdered or freeze-dried compound of the present invention into a vial and sterilizing the vial and its content, which is dissolved in or mixed with carrier just before an administration. In order to make the formulation for parenteral administration isotonic, a non-toxic salt or a salt solution may be added, and solubilizers, preservatives, suspending agents and emulsifying agents may be used together.

The formulation for intrarectal administration may be prepared by kneading the effective component into a hydrophobic or hydrophilic suppository base, e.g., a synthesized oily base such as cacao oil, hydrogenated peanuts oil, hydrogenated coconuts oil, an aqueous base such as polyethylene glycol, monolene, Tween, Pluronic, higher esters (e.g., palmitic acid myristyl ester).

As the formulation for percutaneous administration, plasters, poultices, ointments, gels, creams, gel creams, liniments may be exemplified.

The plasters may be prepared by formulating plaster bases, the effective component and another additives, applying them onto an flexible or non-flexible backing, and applying releasable cover. As the flexible or non-flexible backing, e.g., polypropylene, polyester, polyvinyliden chloride, polyacryl, polyurethane, rayon, cotton, ethylenevinyl acetate copolymer, unwoven fabric and unwoven paper may be exemplified. The plaster bases may be selected and used from known high-molecular bases (e.g., methacrylic esters, acrylonitrile, acrylic compositions which are copolymerized with vinyl monomer such as vinyl acetate and vinyl propionate; silicone resins; polyisoprene rubber; polyisobutylene rubber; natural rubber; acrylic rubber; styrene-isoprene-styrene block copolymer), oil or higher fatty acid (e.g., almond oil, olive oil, camellia oil, Persic oil, peanut oil, oleic acid, liquid paraffin, polybutene), tackifiers (e.g., rosin, rosin modified maleic acid, hydrogenated rosin ester), anti-eruption agent. As another additives, dl-camphor, l-menthol, thymol, vanillyl amide nonylate, capsicum tincture, peppermint oil, UV absorber, antioxidant, may be exemplified. The plasters may be a reservoir type.

The poultices may be prepared by formulating poultice bases, the effective component and another additives appropriately. The poultice bases are selective suitably from, e.g., adhesives (e.g., synthesized water-soluble high-molecular materials such as soda polyacrylate, polyacrylic acid, POVAL, polyvinyl pyrrolidone, polyethylene oxide, polyvinyl methacrylate; natural materials such as gum arabic, starch and gelatin; methylcellulose, hydroxypropylcellulose, alginic acid, sodium alginate, ammonium alginate, sodium carboxymethylcellulose), humectants (e.g., urea, glycerine, propylene glycol, butylene glycol, sorbitol), fillers (e.g., kaoline, zinc oxide, talc, titanium, bentonite, epoxy resins), organic acids (e.g., citric acid, tartaric acid, maleic acid, succinic acid), calcium, magnesium, aluminum and water. In addition, as another additives, e.g., l-menthol, camphor, thymol, peppermint oil, UW absorber and antioxidant are exemplified, and these may be formulated suitably.

The ointments may be prepared by formulating ointment bases, the effective component and another additives appropriately. As the ointment bases, any known bases may be used. The ointment bases may be selected and used from higher fatty acids or esters thereof (e.g., adipic acid, myristic acid, palmitic acid, stearic acid, oleic acid, adipic acid ester, myristic acid ester, palmitic acid ester, diethyl sebacate, hexyl laurate, cetyl isooctate), waxes (e.g., spermaceti, beeswax, ceresin), surfactants (e.g., polyoxyethylene alkylether phosphoric ester), higher alcohols (e.g., cetanol, stearyl alcohol, cetostearyl alcohol), silicone oils (e.g., dimethyl polysiloxane, methylphenyl siloxane, glycolmethyl polysiloxane, silicone glycol copolymer), hydrocarbons (e.g., hydrophilic vaseline, white vaseline, purified lanoline, liquid paraffin), water, humectants (glycerine, propylene glycol, butylene glycol, sorbitol), anti-eruption agent and the like. As another additives, l-menthol, camphor, peppermint oil and the like may be exemplified.

The gels may be prepared by formulating gel bases, the effective component and another additives appropriately. As the gel bases, any known ones may be used, and lower alcohols (e.g., ethanol, isopropyl alcohol), water, gelling agents (e.g., carboxyvinyl polymer, hydroxyethyl cellulose, ethyl cellulose, carboxymethyl cellulose, alginic acid propylene glycol ester), neutralizing agents (e.g., triethanol amine, diisopropanol amine, sodium hydroxide), surfactants (e.g., sorbitan sesquioleate, sorbitan trioleate, sorbitan monooleate, sorbitan monostearate, sorbitan monolaurate, polyethylene glycol monostearate, polyoxyethylene nonylphenyl ether, polyoxyethylene lauryl ether) and anti-eruption agents may be exemplified. These materials may be selected suitably. As another additives, l-menthol, camphor, peppermint oil and the like may be exemplified.

The creams may be prepared by formulating cream bases, the effective component and another additives appropriately. As the cream bases, any known ones may be used, and higher fatty acid esters (e.g., myristic acid esters, palmitic acid esters, diethyl sebacate, hexyl laurate, cetyl isooctate), lower alcohols (e.g., ethanol, isopropanol), hydrocarbons (e.g., liquid paraffin, squalane), polyhydroxy alcohols (e.g., propylene glycol, 1,3-butylene glycol), higher alcohols (e.g., 2-hexyl decanol, cetanol, 2-octyl dodecanol), emulsifiers (e.g., polyoxyethylene alkyl ethers, fatty acid esters, polyethylene glycol fatty acid esters), preservatives (e.g., p-oxy benzoic acid ester) and anti-eruption may be exemplified. These materials may be selected suitably. As another additives, l-menthol, camphor, peppermint oil and the like may be exemplified.

The gel creams which have medium characteristics of the creams and the gels, may be prepared by adding gelling agent (e.g., carboxy vinyl polymers, hydroxyethyl cellulose, hydroxypropyl cellulose, ethyl cellulose, carboxymethyl cellulose) and neutralizing agent (e.g., diisopropanol amine, triethanol amine, sodium hydroxide) to the creams and adjusting pH to 4 to 8, preferably to 5 to 6.5.

The liniments may be prepared by formulating an effective component, UV absorbers, and if necessary, antioxidants, neutralizing agents for the adjustment of pH, tackifiers (e.g., methylcellulose, carboxyvinyl polymer, hydroxypropyl cellulose), anti-eruption agents and another additives (e.g., l-menthol, camphor, peppermint oil, thymol, crotamiton, propylene carbonate, diisopropyl adipate) into alcohols (e.g., monohydroxy alcohols such as ethanol, propanol, isopropanol, polyhydroxy alcohols such as polyethylene glycol, propylene glycol, butylene glycol), water, fatty acid esters (e.g., each ester of adipic acid, sebacic acid, myristic acid) and surfactants (e.g., polyoxyethylene alkyl ether).

The dose of the compound (I), (Ia) or (Ib) or the pharmaceutically acceptable acid addition salt thereof of the present invention is properly determined depending on the conditions, ages, sexes, body weights and the like of the subjects of the administration. However, it is preferable to administer it normally approx. 10 to 500 mg per one time about one to a several times a day when administered for an adult.

Next, a method for preparing the compounds and the pharmaceutically acceptable acid addition salts thereof of the present invention will be explained with an example. The method for preparing the compounds and the pharmaceutically acceptable acid addition salts of the present invention are not limited by the example.

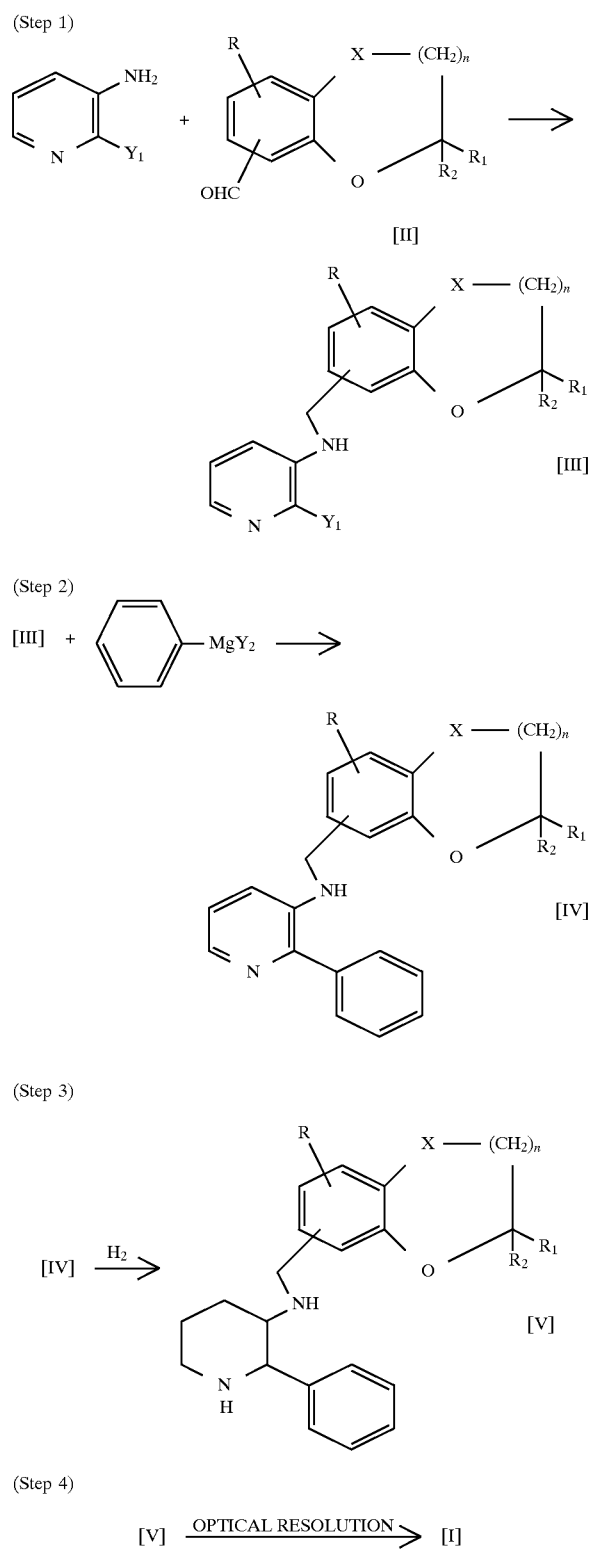

wherein, $Y_1$ represents halogen, mesyl or tosyl, $Y_2$ represents halogen, R, $R_1$, $R_2$, X and n are as defined above.

As shown in above, at the beginning, 3-amino-2-substituted pyridine and formyl compound (II) are reacted in an inactive solvent such as a lower alcohol (e.g., methanol, ethanol) and acetic acid, in the presence of a reducing agent such as cyano sodium borohydride, triacetoxy sodium borohydride and formic acid at 20° to −50° C. to obtain a compound (III) without isolating an imine of intermediate. (The formyl compound (II) can be prepared by the method described in e.g., Yakugakuzasshi,81(3),453–457(1961), Chem.Pharm.Bull.,38(6)1609–1615(1990) and Chem.Pharm.Bull.,42(1)95–100(1994)).

Then, a cross-coupling reaction of the compound (III) thus obtained and Grignard reagent are carried out in an inactive solvent such as tetrahydrofuran (abbreviated as THF, hereinafter) and ether in the presence of a transition-metal catalyst such as {1,2-bis(diphenylphosphino)propane}nickel(II) chloride (abbreviated as $NiCl_2$(dppp), hereinafter) and {1,2-bis(diphenylphosphino)ethane}nickel (II) chloride (abbreviated as $NiCl_2$(dppe), hereinafter) at 0° to 70° C. to obtain the compound (IV).

Then, the compound (IV) thus obtained is hydrogenated in an inactive solvent such as a lower alcohol (e.g., methanol, ethanol) and acetic acid, in the presence of a metal catalyst such as palladium carbon, platinum oxide and Raney-nickel under 1 to 5 atmospheric pressure to obtain a compound (V).

Finally, the racemic mixture (V) is resolved optically to obtain the compound represented by the general formula (I) of the present invention.

Any acid addition salts may be prepared from the free bases. Namely, by mixing the compound (V) and (R)-(−)-mandelic acid in an inactive solvent such as methanol, ethanol or isopropanol and recrystallizing the produced mandelate, a diastereomer salt of (+)isomer having a high optical purity can be prepared. Further, the salt is partitioned between an organic solvent such as ether, chloroform and dichloromethan, and an aqueous inorganic base such as sodium bicarbonate, sodium carbonate and sodium hydroxide to obtain the compound (I) which is (+)enantiomer as free base. Further, by adding e.g., ether containing hydrogen chloride to the free base, an hydrochloride can be prepared.

EXAMPLES

Examples and Test Examples will be described in order to explain the present invention in more detail, hereinafter. The present invention, however, should not be limited by the Examples.

Reference Example 1

5 g of 3-amino-2-chloropyridine was dissolved in 80 ml of acetic acid, and 7.1 g of 2,2-dimethyl-7-formyl-2,3-dihydrobenzofuran was added. Then, the mixture was stirred at room temperature for about 30 minutes, and 16.5 g of triacetoxy sodium borohydride was added gradually under ice-cooling. After stirring the obtained reaction mixture at room temperature for about four hours, the solvent was concentrated. After adding ice-water to the residue and alkalizing it with an aqueous sodium hydroxide solution, it was extracted twice with ethyl acetate. After washing the organic layer with water and drying, it was concentrated and purified with a short column (dichloromethane/methanol= 10:1) using silica gel to obtain 12.2 g of oily 3-[(2,2-dimethyl-2,3-dihydrobenzofuran-7-yl)methyl]amino-2-chloropyridine.

MS 119,161(base),288(M+); NMR($CDCl_3$) 1.48(6H,s), 3.00(2H,s),4.32(2H,bs),5.06(1H,br); 6.78(1H,t,J=7.5 Hz), 6.93–7.07(4H,m), 7.68(1H,dd, J=4.6 Hz,J=1.7 Hz)

Reference Example 2

12 g of 3-[(2,2-dimethyl-2,3-dihydrozenbofuran-7-yl)methyl]amino-2-chloropyridine was dissolved in approx. 400 ml of anhydrous THF, and 7.8 g of $NiCl_2$ (dppe) was added. 30 ml of 3M ether solution of phenylmagnesium bromide was added dropwise to the mixture with stirring at room temperature under nitrogen flow, and a reaction was carried out for seven hours. Further, 20 ml of 3M ether solution of phenylmagnesium bromide was added and kept stirring for 15 hours. After completion of the reaction, the reaction mixture was poured into a mixed liquid of 600 ml of conc.HCl and approx. 400 ml of ice-water, and washed with approx. 500 ml of ethyl acetate. After alkalizing the acid water layer with 50% aqueous sodium hydroxide solution with cooling, approx. 1000 ml of ethyl acetate was added and Celite was added with stirring. After the precipitates were filtered off, it was washed with 500 ml of ethyl acetate twice. The organic layer was separated, and the aqueous layer was extracted with ethyl acetate. These were combined and dried with magnesium sulfate. The residue which was obtained by distilling off the solvent, was purified by a silica gel column chromatography (isopropyl ether/hexane=1:1-isopropyl ether-isopropyl ether/ethyl acetate= 1:1) to obtain 9.4 g of oily 3-[(2,2-dimethyl-2,3-dihydrobenzofuran-7-yl)methyl]amino-2-phenylpyridine.

MS 119,161(base),330(M+); NMR($CDCl_3$) 1.38(6H,s), 2.96(2H,s),4.23(2H,d,J=5.9 Hz),4.76(1H,br), 6.75(1H,t,J= 7.5 Hz),7.01–7.09(4H,m),7.32–7.47 (3H,m),7.63–7.67(2H, m),8.02(1H,dd,J=4.4 Hz, J=1.8 Hz)

Reference Example 3

From 24 g of 7-ethoxycarbonyl-2-methyl-2,3-dihydrobenzofuran, 11.8 g of the former component (99.5% e.e.) and 11.6 g of the latter component (99.7% e.e.) of the optical isomers derived from methyl group in the 2-position under the following conditions.

Column: Chiral Cell OJ (Daicell)
Mobil phase: Hexane/2-propanol/acetic acid=90:10:0.3

After adding dropwise 11 g of each ester in 100 ml of anhydrous THF containing 2.2 g of lithium aluminum hydride at 0° C. under nitrogen flow, the mixture was stirred at room temperature for one hour. After completion of the reaction, ice pieces were added carefully to decompose the excessive reducing agent. Then, excessive magnesium sulphate was added and the solid materials were filtered off. The residue which was obtained by concentrating the solvent under reduced pressure, was purified by a silica gel column (isopropyl ether/hexane=1:2) to obtain 8.4 g (derived from the former component) and 8.5 g (derived from the latter component) of each corresponding 7-hydroxymethyl-2-methyl-2,3-dihydrobenzofuran were prepared.

Into a solution obtained by dissolving 8.3 g of oxalyl chloride in 30 ml of methylene chloride, a solution obtained by dissolving 8.7 g of dimethyl sulfoxide in 5 ml of methylene chloride was added dropwise at −78° C. under nitrogen flow. Further, after stirring at the same temperature for one hour, 25 g of triethyl amine was added and left to warm up to room temperature. Cold water was added to the reaction solution, and the organic phase was separated. After washing with water and drying, the solvent was concentrated under reduced pressure. The residue was purified with a silica gel column (hexane-hexane/isopropyl ether=2:1) to obtain 7.9 g (the former component) and 7.8 g (the latter component) of each corresponding 7-formyl-2-methyl-2,3-dihydrobenzofuran.

| | |
|---|---|
| Enantiomer A (the former component) | m.p. 47–48.5° C.<br>NMR(CDCl$_3$)1.53(3H,d,<br>J=6.23 Hz) |
| Enantiomer B (the latter component) | m.p. 47.5–49° C.<br>NMR(CDCl$_3$)1.53(3H,d,<br>J=6.23 Hz) |

The enantiomers of the following Reference Examples 4 to 6, based on Reference Example 3.

Reference Example 4
5-chloro-2-methyl-7-formyl-2,3-dihydrobenzofuran

| | |
|---|---|
| Enantiomer A (the former component) | m.p. 54–55° C.<br>NMR(CDCl$_3$)1.53(3H,d,<br>J=6.22 Hz) |
| Enantiomer B (the latter component) | m.p. 54.5–56° C.<br>NMR(CDCl$_3$)1.53(3H,d,<br>J=6.23 Hz) |

Reference Example 5
5-methoxy-2-methyl-7-formyl-2,3-dihydrobenzofuran

| | |
|---|---|
| Enantiomer A (the former component) | m.p. 86–87.5° C.<br>NMR(CDCl$_3$)1.51(3H,d,<br>J=6.22 Hz) |
| Enantiomer B (the latter component) | m.p. 57–88.5° C.<br>NMR(CDCl$_3$)1.52(3H,d,<br>J=6.22 Hz) |

Reference Example 6
2,5-dimethyl-7-formyl-2,3-dihydrobenzofuran

| | |
|---|---|
| Enantiomer A (the former component) | oily material<br>NMR(CDCl$_3$)1.52(3H,d,<br>J=6.23 Hz) |
| Enantiomer B (the latter component) | oily material<br>NMR(CDCl$_3$)1.53(3H,d,<br>J=6.23 Hz) |

Example 1

9.2 g of 3-[(2,2-dimethyl-2,3-dihydrobenzofuran-7-yl)methyl]amino-2-phenylpyridine was dissolved in 120 ml of acetic acid, and 1 g of platinum oxide was added. A hydrogenation reaction was carried out at 3 atmospheric pressure for 8.5 hours. After completion of the reaction, the catalyst was filtered off and the solvent was concentrated. After adding ice pieces to the residue and alkalizing it with 50% aqueous sodium hydroxide solution, it was extracted three times with dichloromethane. After drying the extract solution, it was distilled off and purified by a silica gel chromatography (dichloromethane/methanol 30:1-10:1-3:1) to obtain 3.7 g of oily 3-[(2,2-dimethyl-2,3-dihydrobenzofuran-7-yl)methyl]amino-2-phenylpiperidine.

MS 161(base),176,217,336(M+)

Example 2

3.63 g of 3-[2,2-dimethyl-2,3-dihydrobenzofuran-7-yl)methyl]amino-2-pheynylpiperidine which was prepared in Example 1, was dissolved in 15 ml of methanol. About 15 ml of a methanol solution containing 1.64 g of (R)-(−)-mandelic acid was added, and stirred at room temperature for 10 minutes. The residue obtained by concentrating and solidifying methanol, was crystallized with ether, and the crystals were obtained by filtration. The crystals were washed with a small amount of isopropanol and then with ether to obtain 3.2 g of crude crystals. The obtained diastereomer salt was recrystallized with isopropanol to obtain 2.5 g of a salt showing [α]D=+6.8(methanol, C=0.49). Further, it was recrystallized with isopropanol to obtain a salt showing [α]D=+7.1(methanol, C=0.48). The obtained diastereomer salt was partitioned into 1M aqueous sodium hydroxide solution and dichloromethane, and extracted three times with 10 ml of dichloromethane under alkaline condition. After drying the organic layer, it was concentrated to solidify, an oily free base was obtained. After adding 1 ml of dichloromethane to it, the crystals which were obtained by adding ether containing hydrogen chloride dropwise, were obtained by filtration. The crystals were recrystallized with ethanol to obtain 1.9 g of (2S,3S)-3-[(2,2-dimethyl-2,3-dihydrobenzofuran-7-yl)methyl]amino-2-phenylpiperidine hydrochloride.

m.p. 231°–235° C.(dec.); MS 70,161(base),176,217,336 (M+); NMR(DMSO-d$_6$) 1.38(3H,s),1.39(3H,s),1.79–1.84 (1H,m), 2.11–2.28 (2H,m),2.35–2.40(1H,m),2.97(2H,s), 3.13–3.21(1H,m),3.42(1H,d,J=13.6 Hz), 3.43–3.49(1H,m), 3.67(1H,d,J=13.6 Hz),3.97(1H,bs),4.99(1H,bs),6.76(1H, t,J=7.5 Hz),7.13–7.21(2H,m),7.43–7.55(3H,m),7.74–7.76 (2H,m),9–10(2H,br),10.59(2H,br); Elemental Analysis (C$_{22}$H$_{28}$N$_2$O.2HCl); Calculated C:64.54 H:7.39 N:6.84; Found C:64.38 H:7.31 N:6.86

According to the steps described in Reference Example 1—Reference Example 2—Example 1—Example 2, the following compounds were prepared. As to Examples 3, 14, 15 and 22, enantiomers (Reference Examples 3, 4, 5 and 6) of 7-formyl-2-methyl-2,3-dihydrobenzofurans which were prepared based on Reference Example 3, were prepared as raw materials for preparation of epimers derived from mono-methyl group in the 2-position, based on the above steps.

Example 3
(2S,3S)-3-[(2-methyl-2,3-dihydrobenzofuran-7-yl)methyl]amino-2-phenylpiperidine hydrochloride m.p. 228°–231° C.(dec.); MS 70,147(base),162,203,322 (M+); NMR(DMSO-d$_6$) 1.33–1.38(3H,m),1.78–1.84 (1H,m),2.11–2.44(3H,m), 2.69–2.78(1H,m),3.13–3.48(4H, m),3.69–3.76(1H,m), 3.93–3.99(1H,m),4.81–4.91(1H,m), 4.98(1H,bs), 6.76(1H,t,J=7.5 Hz),7.14–7.25(2H,m), 7.42–7.53(3H, m),7.72–7.77(2H,m),9–10(2H,br),10.69(2H, br); Elemental Analysis (C$_{21}$H$_{26}$N$_2$O.2HCl); Calculated C:63.80 H:7.14 N:7.09; Found C:63.54 H:7.19 N:6.95

Example 3A
(Preparation of epimer 3A from enantiomer A of Reference Example 3)

(2S,3S)-3-[(2-methyl-2,3-dihydrobenzofuran-7-yl)methyl]amino-2-phenylpiperidine hydrochloride m.p. 245°–258° C.(dec.); MS 70,147(base),162,203,322 (M+); NMR(DMSO-d$_6$) 1.33(3H,d,J=5.86 Hz); Elemental Analysis (C$_{21}$H$_{26}$N$_2$O.2HCl); Calculated C:63.80 H:7.14 N:7.09; Found C:63.84 H:7.20 N:7.14

Example 3B
(Preparation of epimer 3B from enantiomer B of Reference Example 3)

(2S,3S)-3-[(2-methyl-2,3-dihydrobenzofuran-7-yl)methyl]amino-2-phenylpiperidine hydrochloride m.p. 250°–263° C.(dec.); MS 70,147(base),162,203,322 (M+); NMR(DMSO-d$_6$) 1.36(3H,d,J=6.22 Hz); Elemental Analysis (C$_{21}$H$_{26}$N$_2$O.2HCl); Calculated C:63.80 H:7.14 N:7.09; Found C:63.86 H.7.13 N:7.07

Example 4
(2S,3S)-3-[(2,2-dimethyl-5-nitro-2,3-dihydrobenzofuran-7-yl)methyl]amino-2-phenylpiperidine hydrochloride m.p. 239°–256° C.(dec.); MS 70(base),206,245,262,364, 382(M+1); NMR(DMSO-d$_6$) 1.44(3H,s),1.47(3H,s), 1.80–1.85(1H,m),2.04–2.26(2H,m),2.37–2.41(1H,m),3.09 (2H,s),3.12–3.20(1H, m),3.44(1H,d,J=13.8 Hz),3.43–3.47 (1H,m),3.77(1H, d,J=13.8 Hz),3.88(1H,br),4.92(1H,bs), 7.47(3H,m), 7.70(2H,m),8.05(1H,d,J=2.4 Hz),8.24(1H,d,J= 2.0 Hz), 9–10(2H,br),10.29(2H,br); Elemental Analysis (C$_{22}$H$_{27}$N$_3$O$_3$.2HCl); Calculated C:58.15 H:6.43 N:9.25; Found C:58.15 H:6.44 N:9.16

Example 5
(2S,3S)-3-[(2,2-dimethyl-5-methylthio-2,3-dihydrobenzofuran-7-yl)methyl]amino-2-phenylpiperidine hydrochloride m.p. 221°–225° C.(dec.); MS 207(base),263,382(M+); NMR(DMSO-d$_6$) 1.37(3H,s),1.38(3H,s),2.41(3H,s),2.96 (2H,s), 1.78–1.84(1H,m),2.04–2.27(2H,m),2.33–2.38(1H, m), 3.12–3.20(1H,m),3.39(1H,d,J=13.9 Hz),3.43–3.49(1H, m),3.66(1H,d,J=13.9 Hz),3.91(1H,bs),4.95(1H, bs),7.12 (1H,d,J=1.8 Hz),7.20(1H,d,J=1.8 Hz),7.43–7.55(3H,m), 7.71–7.74(2H,m),9–10(2H,br),10.39(2H,br); Elemental analysis (C$_{23}$H$_{30}$N$_2$SO.2HCl); Calculated C:60.65 H:7.08 N:6.15; Found C:60.58 H:7.13 N:6.18

Example 6
(2S,3S)-3-[(2,2-dimethyl-5-methylsulfonyl-2,3-dihydrobenzofuran-7-yl)methyl]amino-2-phenylpiperidine hydrochloride m.p. 230°–256° C.(dec.); MS 70(base),175,239,295,414 (M+); NMR(DMSO-d$_6$) 1.43(3H,s),1.44(3H,s),1.80–1.85 (1H,m),2.07–2.27(2H,m),2.41–2.46(1H,m),3.07(2H,s),3.13 (3H,s),3.14–3.21(1H,m),3.39(1H,d,J=13.9 Hz),3.42–3.48 (1H,m), 3.76(1H,d=13.9 Hz),3.97(1H,br),4.98(1H,bs), 7.43–7.55 (3H,m),7.67(1H,d,J=1.8 Hz),7.73–7.76(2H,m), 7.88(1H,d,J=1.8 Hz),9–10(2H,br),10.54(2H,br); Elemental Analysis (C$_{23}$H$_{30}$N$_2$SO$_3$.2HCl.0.25H$_2$O); Calculated C:56.15 H:6.66 N:5.69; Found C:56.09 H:6.68 N:5.78

Example 7
(2S,3S)-3-[(2,2-dimethyl-5-dimethylaminosulfonyl-2,3-dihydrobenzofuran-7-yl)methyl]amino-2-phenylpiperidine hydrochloride m.p. 246°–250° C.(dec.); MS 70(base),175,268,443(M+); NMR(DMSO-d$_6$) 1.43(6H,s),1.79–1.84(1H,m),2.08–2.38 (3H,m),2.59(6H,s),3.07(2H,s),3.12–3.20(1H,m),3.41–3.47 (1H, m),3.51(1H,d,J=13.9 Hz),3.75(1H,d,J=13.9 Hz),3.84 (1H,br),4.91(1H,bs),7.43–7.54(4H,m),7.65–7.71(3H,m), 9–10(2H,br),10.21(2H,br); Elemental Analysis (C$_{24}$H$_{33}$N$_3$SO$_3$.2HCl); Calculated C:55.81 H:6.83 N:8.14; Found C:55.77 H:6.76 N:8.07

Example 8
(2S,3S)-3-[(5-dimethlaminosulfonyl-2-methyl-2,3-dihydrobenzofuran-7-yl)methyl]amino-2-phenylpiperidine hydrochloride m.p. 236°–240° C.(dec.); MS 70(base),175,254,429(M+); NMR(DMSO-d$_6$) 1.40–1.43(3H,m),1.81–1.91(1H,m), 2.08–2.43(3H,m), 2.60(6H,s),2.80–2.89(1H,m),3.13–3.22 (1H,m),3.35–3.53(3H,m),3.78–3.85(1H,m),3.91–3.96(1H, m),4.96–5.11(2H,m),7.42–7.53(4H,m),7.69–7.75(3H,m), 9–10(2H,br),10.61(2H,br); Elemental Analysis (C$_{23}$H$_{31}$N$_3$SO$_3$.2HCl); Calculated C:54.98 H:6.62 N:8.36; Found C:54.98 H:6.73 N:8.36

Example 9
(2S,3S)-3-(3,4-methylenedioxybenzyl)amino-2-phenylpiperidine hydrochloride m.p. 257°–260° C.(dec.); MS 70,135(base),191,310(M+); NMR(DMSO-d$_6$) 1.79–1.84(1H,m),2.04–2.29(2H,m),2.43 (1H,br),3.13–3.21(1H,m),3.25(1H,d,J=13.0 Hz),3.45–3.50 (1H,m), 3.63(1H,d,J=13.0 Hz),3.90(1H,bs),4.96(1H,bs), 5.99(2H,s),6.67(1H,dd,J=7.9 Hz,J=1.7 Hz),6.83(1H,d, J=7.9 Hz), 6.96(1H,d,J=1.7 Hz),7.45–7.58(3H,m), 7.75–7.78(2H, m), 9.57(2H,br),10.49(2H,br); Elemental Analysis (C$_{19}$H$_{22}$N$_2$O$_2$.2HCl); Calculated C:59.54 H:6.31 N:7.31; Found C:59.31 H:6.42 N:7.31

Example 10
(2S,3S)-3-[(3,4-dihydro-1,2-benzopyran-8-yl)methyl] amino-2-phenylpiperidine hydrochloride m.p. 255°–258° C.(dec.); MS 70,147(base),203,322(M+); NMR(DMSO-d$_6$) 1.78–1.90(3H,m),2.09–2.14(1H,m), 2.21–2.37(2H, m),2.67(2H,t,J=6.4 Hz),3.13–4.49(2H,m),3, 44(1H, d,J=13.0 Hz),3.80(1H,d,J=13.0 Hz),3.90(1H,bs), 3.95–4.13(2H,m),4.93(1H,bs),6.76(1H,t,J=7.6 Hz), 7.04 (2H,d,J=7.6 Hz),7.44–7.56(3H,m),7.70–7.73(2H,m), 8.2–9.7(2H,br),10.18(2H,br); Elemental Analysis (C$_{21}$H$_{26}$N$_2$O.2HCl); Calculated C:63.80 H:7.14 N:7.09; Found C:63.54 H:7.06 N:7.11

Example 11
(2S,3S)-3-[(5-chloro-2,2-dimethyl-2,3-dihydrobenzofuran-7-yl)methyl]amino-2-phenylpiperidine hydrochloride m.p. 220°–231° C.(dec.); [α]D=+112.28 (c=0.51, methanol); MS 70(base),195,251,370(M+); NMR(DMSO-d$_6$) 1.34(3H,s),1.38(3H,s),1.70–1.76(1H,m),1.90–2.24(3H, m),2.95(2H,s),3.04–3.64(5H,m),4.73(1H, br),7.14(2H,bs), 7.41–7.58(5H,m),8.5–9.5(2H,br), 9.58(2H,br); Elemental Analysis (C$_{22}$H$_{27}$ClN$_2$O.2HCl); Calculated C:59.53 H:6.59 N:6.31; Found C:59.31 H:6.57 N:6.37

Example 12
(2S,3S)-3-[(2,2-dimethyl-5-methoxy-2,3-dihydrobenzofuran-7-yl)methyl]amino-2-phenylpiperldine hydrochloride m.p. 207°–216° C.(dec.); MS 70,191(base),206,247,366 (M+); NMR(DMSO-d$_6$) 1.35(3H,s),1.36(3H,s),1.78–1.83 (1H,m),2.07–2.36(3H,m),2.93(2H,s),3.12–3.21(1H,m), 3.38–3.49(1H,m),3.40(1H,d,J=13.6 Hz),3.66(1H,d,J=13.6 Hz),3.67(3H,s),3.91(1H,br),4.94(1H,bs), 6.77(1H,d,J=2.6 Hz),6.84(1H,d,J=2.6 Hz),7.43–7.55(3H,m),7.71–7.74(2H, m),8.7–9.9(2H,br), 10.27(2H,br); Elemental Analysis (C$_{23}$H$_{30}$N$_2$O$_2$.2HCl); Calculated C:62.87 H:7.34 N:6.38; Found C:62.68 H:7.29 N:6.44

Example 13
(2S,3S)-3-[(2,3-dihydrobenzofuran-7-yl)methyl]amino-2-phenylpiperidine hydrochloride m.p. 228°–234° C.(dec.); MS 70,133(base),189,308(M+); NMR(DMSO-d$_6$) 1.76–1.81(1H,m),2.04–2.32(3H,m), 3.10–3.49(5H, m),3.75(2H,d,J=13.6 Hz),4.45(2H,t,J=8.8 Hz), 4.87(1H,bs),6.77(1H,t,J=7.5 Hz),7.10–7.19(2H,m), 7.43–7.55(3H,m),7.66–7.69(2H,m),8.3–9.4(2H,br),9.96 (2H,br); Elemental Analysis (C$_{20}$H$_{24}$N$_2$O.2HCl.1.25H$_2$O); Calculated C:59.48 H:7.11 N:6.94; Found C:59.67 H:7.03 N:7.07

Example 14
(2S,3S)-3-[(5-chloro-2-methyl-2,3-dihydrobenzofuran-7-yl) methyl]amino-2-phenylpiperidine hydrochloride m.p. 243°–251° C.(dec.); [α]D=+56.27 (c=0.51, methanol); MS 70,181(base),237,356(M+); NMR(DMSO- $d_6$) 1.32–1.35(3H,m),1.77–1.82(1H,m),2.04–2.33(3H, m),2.70–2.79(1H,m),3.08–3.48(5H,m),3.69–3.74(1H,m), 4.86–4.94(2H,m),7.19–7.25(2H,m),7.42–7.54(3H,m), 7.64–7.67(2H,m),8.2–9.8(2H,br),10.01(2H,br); Elemental Analysis ($C_{21}H_{25}ClN_2O.2HCl$); Calculated C:58.68 H:6.33 N:6.52; Found C:58.55 H:6.31 N:6.61

Example 14A
(Preparation of epimer 14A from enantiomer A of Reference Example 4)

(2S,3S)-3-[(5-chloro-2-methyl-2,3-dihydrobenzofuran-7-yl)methyl]amino-2-phenylpiperidine hydrochloride m.p. 228°–242° C.(dec.); MS 70,181(base),237,356(M+); NMR(DMSO-$d_6$) 1.34(3H,d,J=6.23 Hz); Elemental Analysis ($C_{21}H_{25}ClN_2O.2HCl$); Calculated C:58.68 H:6.33 N:6.52; Found C:58.65 H:6.29 N:6.60

Example 14B
(Preparation of epimer 14B from enantiomer B of Reference Example 4)

(2S,3S,)-3-[(5-chloro-2-methyl-2,3-dihydrobenzofuran-7-yl)methyl]amino-2-phenylpiperidine hydrochloride m.p. 249°–261° C.(dec.); MS 70,181(base),237,356(M+); NMR(DMSO-$d_6$) 1.32(3H,d,J=5.86 Hz)); Elemental Analysis ($C_{21}H_{25}ClN_2O.2HCl$); Calculated C:58.68 H:6.33 N:6.52; Found C:58.72 H:6.27 N:6.48

Example 15
(2S,3S)-3-[(5-methoxy-2-methyl-2,3-dihydrobenzofuran-7-yl)methyl]amino-2-phenylpiperidine hydrochloride m.p. 214°–223° C.(dec.); MS 70,177(base),192,233,352 (M+); NMR(DMSO-$d_6$) 1.30–1.34(3H,m),1.77–1.82(1H,m) ,2.06–2.34(3H,m), 2.66–2.75(1H,m),3.12–3.49(4H,m),3.67 (3H,s),3.73–3.75(1H,m),3.79–3.93(1H,m),4.74–4.85(1H, m),4.91(1H,bs),6.77–6.84(2H,m),7.43–7.55(3H,m),7.70 (2H, br),9–10(2H,br),10.12(2H,br); Elemental Analysis ($C_{22}H_{28}N_2O_2.2HCl$); Calculated C:62.12 H:7.11 N:6.59; Found C:62.27 H:7.09 N:6.76

Example 15A
(Preparation of epimer 15A from enantiomer A of Reference Example 5)

(2S,3S)-3-[(5-methoxy-2-methyl-2,3-dihydrobenzofuran-7-yl)methyl]amino-2-phenylpiperidine hydrochloride m.p. 208°–216° C.(dec.); MS 70,177(base),192,233,352 (M+); NMR(DMSO-$d_6$) 1.31(3H,d,J=6.23 Hz); Elemental Analysis ($C_{22}H_{28}N_2O_2.2HCl$); Calculated C:62.12 H:7.11 N:6.59; Found C:62.09 H:7.13 N:6.64

Example 15B
(Preparation of epimer 15B from enantiomer B of Reference Example 5)

(2S,3S)-3-[(5-methoxy-2-methyl-2,3-dihydrobenzofuran-7-yl)methyl]amino-2-phenylpiperidine hydrochloride m.p. 217°–226° C.(dec.); MS 70,177(base),192,233,352 (M+); NMR(DMSO-$d_6$) 1.34(3H,d,J=5.86 Hz); Elemental Analysis ($C_{22}H_{28}N_2O_2.2HCl$); Calculated C:62.12 H:7.11 N:6.59; Found C:62.08 H:7.16 N:6.52

Example 16
(2S,3S)-3-[2,2,4-trimethyl-2,3-dihydrobenzofuran-7-yl) methyl]amino-2-phenylpiperidine hydrochloride m.p. 213°–217° C.(dec.); MS 175(base),350(M+); NMR (CDCl$_3$) 1.27(3H,s),1.32(3H,s),1.55(1H,bs),2.16(3H,s), 2.33(3H,bs),2.84(2H,s),3.17(1H,br),3.38(1H,m), 3.62–3.74 (3H,m),5.57(1H,bs),6.57(1H,d,J=7.9 Hz), 6.78(1H,d,J=7.9 Hz),7.36–7.46(H,m),7.69(2H,dd, J=8.1 Hz, J=1.8 Hz), 9.85–10.28(2H,br),11.42(2H,br); Elemental Analysis ($C_{23}H_{30}N_2O.H_2O$); Calculated C:62.58 H:7.76 N:6.35; Found C:62.87 H:7.81 N:6.44

Example 17
(2S,3S)-3-[(2,2,5-trimethyl-2,3-dihydrobenzofuran-7-yl) methyl]amino-2-phenylpiperidine hydrochloride m.p. 217°–221° C.(dec.); MS 175(base),350(M+); NMR (DMSO-$d_6$) 1.36(6H,s),1.78–1.83(1H,m),2.17(3H,s), 2.08–2.33(3H,m),2.92(2H,s),3.13–3.63(4H,m),3.89(1H, bs),4.93(1H,bs),6.91(1H,s),6.95(1H,s),7.44–7.55(3H,m), 7.72(2H,d,J=6.6 Hz),9–10(2H,br), 10.18(2H,br); Elemental Analysis ($C_{23}H_{30}N_2O.2HCl$); Calculated C:65.24 H:7.62 N:6.62; Found C:65.20 H:7.81 N:6.64

Example 18
(2S,3S)-3-[(4-chloro-2,2-dimethyl-2,3-dihydrobenzofuran-7-yl)methyl]amino-2-phenylpiperidine hydrochloride m.p. 216°–225° C.(dec.); MS 195(base),370(M+); NMR (DMSO-$d_6$) 1.42(6H,s),1.78–1.83(1H,m),2.03–2.37(3H,m), 3.01(2H,s),3.12–3.48(3H,m),3.65(1H,d,J=13.6 Hz), 3.89 (1H,bs),4.92(1H,bs),6.83(1H,d,J=8.1 Hz), 7.23(1H,d,J=8.1 Hz),7.43–7.54(3H,m),7.71(2H,d, J=6.6 Hz),9–10(2H,br), 10.25(2H,br); Elemental Analysis ($C_{22}H_{27}ClN_2O.2HCl$); Calculated C:59.54 H:6.59 N:6.31; Found C:59.72 H:6.60 N:6.46

Example 19
(2S,3S)-3-(3,4-ethylenedioxybenzyl)amino-2-phenylpiperidine hydrochloride m.p. 231°–244° C.(dec.); MS 149(base),324(M+); NMR (DMSO-$d_6$) 1.79–1.84(1H,m),2.03–2.28(2H,m),2.38–2.43 (1H, m),3.13–3.60(4H,m),3.88(1H,bs),4.20(4H,s), 4.95(1H, bs),6.67–6.86(3H,m),7.45–7.56(3H,m), 7.76(2H,d,J=7.0 Hz),9–10(2H,br),10.43(2H,br); Elemental Analysis ($C_{20}H_{24}N_2O_2.2HCl$); Calculated C:60.46 H:6.60 N:7.05; Found C:60.46 H:6.62 N:7.10

Example 20
(2S,3S)-3-[(2,3-dimethyl-2,3-dihydrobenzofuran-7-yl) methyl]amino- 2-phenylpiperidine hydrochloride m.p. 231°–235° C.(dec.); Ms 161(base),336(M+); NMR (DMSO-$d_6$) 1.24(3H,d,J=6.6 Hz),1.36(3H,d,J=5.9 Hz), 1.78–1.83(1H,m),2.03–2.35(3H,m),2.94–3.05(1H,m), 3.12–3.21(1H,m),3.33–3.49(2H,m),3.73–3.78(1H, m),3.87 (1H,br),4.25–4.32(1H,m),4.92(1H,bs), 6.76–6.83(1H,m), 7.12–7.19(2H,m),7.43–7.55(3H, m),7.71(2H,d,J=6.2 Hz), 9–10(2H,br),10.19(2H,br); Elemental Analysis ($C_{22}H_{28}N_2O.2HCl$); Calculated C:64.54 H:7.39 N:6.84; Found D:64.60 H:7.18 N:6.93

Example 21
(2S,3S)-3-[(2,3,4-trimethyl-2,3-dihydrobenzofuran-7-yl) methyl]amino-2-phenylpiperidine hydrochloride m.p. 231°–237° C.(dec.); MS 175(base),350(M+); NMR (DMSO-$d_6$) 0.96–0.99(3H,m),1.33–1.37(3H,m),1.77–1.83 (1H, m),1.98–2.38(3H,m),2.22(3H,s),3.01–3.48(4H,m), 3.67–3.72(1H,m),3.89(1H,br),4.62–4.75(1H,m), 4.93(1H, bs),6.60(1H,d,J=8.0 Hz),7.07(1H,dd, J=8.0 Hz,J=1.7 Hz), 7.43–7.54(3H,m),7.72–7.74(2H, m),8.7–9.7(2H,br),10.29 (2H,br); Elemental Analysis ($C_{23}H_{30}N_2O.2HCl$); Calculated C:65.24 H:7.62 N:6.62; Found C:65.32 H:7.49 N:6.66

Example 22A
(Preparation of epimer 22A from enantiomer A of Reference Example 6)

(2S,3S)-3-[(2,5-dimethyl-2,3-dihydrobenzofuran-7-yl) methyl]amino-2-phenylpiperidine hydrochloride m.p. 228°–245° C.(dec.); MS 70,161(base),336(M+); NMR(DMSO-$d_6$) 1.32(3H,d,J=6.23 Hz); Elemental Analysis ($C_{22}H_{28}N_2O.2HCl$); Calculated C:64.54 H:7.39 N:6.84; Found C:64.51 H:7.38 N:6.91

Example 22B
(Preparation of epimer 22B from enantiomer B of Reference Example 6)
(2S,3S)-3-[(2,5-dimethyl-2,3-dihydrobenzofuran-7-yl)methyl]amino-2-phenylpiperidine hydrochloride m.p. 230°–248° C.(dec.); MS 70,161(base),336(M+); NMR(DMSO-$d_6$) 1.30(3H,d,J=6.23 Hz); Elemental Analysis ($C_{22}H_{28}N_2O.2HCl$); Calculated C:64.54 H:7.39 N:6.84; Found C:64.51 H:7.31 N:6.94

Example 23
(2S,3S)-3-[(5-isopropyl-2,3-dihydrobenzofuran-7-yl)methyl]amino-2-phenylpiperidine hydrochloride m.p. 204°–220° C.(dec.); NMR(DMSO-$d_6$) 1.16(6H,d,J=6.96 Hz, —CH3—(i-Pr)),2.72–2.82(1H, m, —CH=),7.07 (2H,s,Ar-H),7.42–7.54(3H,m,Ar-H), 7.72–7.74(2H,m,Ar-H); Elemental Analysis ($C_{23}H_{30}N_2O.2HCl$); Calculated C:65.24 H:7.62 N:6.62; Found C:65.17 H:7.58 N:6.61

Example 24
(2S,3S)-3-[(5-tert-butyl-2,3-dihydrobenzofuran-7-yl)methyl]amino-2-phenylpiperidine hydrochloride m.p. 190°–205° C.(dec.); NMR(DMSO-$d_6$) 1.24(9H,s,t-Bu),7.23(2H,s,Ar-H),7.42–7.54(3H, m,Ar-H),7.73–7.75 (2H,m,Ar-H); Elemental Analysis ($C_{24}H_{32}N_2O.2HCl$); Calculated C:65.90 H:7.83 N:6.40; Found C:65.64 H:7.92 N:6.36

Example 25
(2S,3S)-3-[(5-cyclopentyl-2,3-dihydrobenzofuran-7-yl)methyl]amino-2-phenylpiperidine hydrochloride m.p. 194°–201° C.(dec.); NMR(DMSO-$d_6$) 1.45–1.97 (8H,m, —CH2—(cyclo-pentyl)),2,79–2.92(1H,m, —CH=),7.07–7.09(2H,m,Ar-H),7.42–7.53(3H, m,Ar-H), 7.72–7.75(2H,m,Ar-H); Elemental Analysis ($C_{25}H_{32}N_2O.2HCl$); Calculated C:66.81 H:7.62 N:6.23; Found C:66.15 H:7.59 N:6.19

Example 26
(2S,3S)-3-[(5-cyclohexyl-2,3-dihydrobenzofuran-7-yl)methyl]amino-2-phenylpiperidine hydrochloride m.p. 190°–205° C.(dec.); NMR(DMSO-$d_6$) 1.17–1.43 (5H,m, —CH2—(cyclo-hexyl)),1.68–1.83(5H,m, —CH2—(cyclo-hexyl)),7.04(2H,s,Ar-H), 7.42–7.54(3H,m,Ar-H), 7.71–7.73(2H,m,Ar-H); Elemental Analysis ($C_{26}H_{34}N_2O.2HCl.0.25H_2O$); Calculated C:66.73 H:7.86 N:5.99; Found C:66.83 H:7.85 N:5.98

Example 27
(2S,3S)-3-[(5-ethylthio-2,3-dihydrobenzofuran-7-yl)methyl]amino-2-phenylpiperidine hydrochloride m.p. 206°–227° C.(dec.); NMR(DMSO-$d_6$) 1.18(3H,t,J=7.33 Hz,CH3—),2.86(2H,q,J=7.33 Hz), —CH2—),7.20 (1H,s,Ar-H),7.27(1H,s,Ar-H),7.42–7.53(3H,m,Ar-H), 7.73–7.74(2H,m,Ar-H); Elemental Analysis ($C_{22}H_{28}N_2OS.2HCl$); Calculated C:59.86 H:6.85 N:6.35; Found C:59.92 H:6.87 N:6.23

Example 28
(2S,3S)-3-[(5-isopropylthio-2,3-dihydrobenzofuran-7-yl)methyl]amino-2-phenylpiperidine hydrochloride m.p. 188°–198° C.(dec.); NMR(DMSO-$d_6$) 1.19(6H,d, 7.33 Hz, —CH3—(i-Pr)),3,20–3.30(1H,m, —CH=), 7.23–7.30(2H,m,Ar-H),7.42–7.54(3H,m,Ar-H), 7.69–7.72 (2H,m,Ar-H); Elemental Analysis ($C_{23}H_{30}N_2OS.2HCl$); Calculated C:60.65 H:7.08 N:6.15; Found C:60.50 H:7.08 N:6.04

Example 29
(2S,3S)-3-[(5-cyclohexylthio-2,3-dihydrobenzofuran-7-yl)methyl]amino-2-phenylpiperidine hydrochloride m.p. 203°–220° C.(dec.); NMR(DMSO-$d_6$) 1.06–1.37 (5H,m,cyclo-pentyl),1.52–1.91(6H,m, cyclo-pentyl),7.22 (1H,s,Ar-H),7.31(1H,s,Ar-H), 7.42–7.53(3H,m,Ar-H), 7.72–7.73(2H,m,Ar-H); Elemental Analysis ($C_{26}H_{34}N_2OS.2HCl$); Calculated C:63.02 H:7.33 N:5.65; Found C:63.09 H-7.36 N:5.58

Example 30
(2S,3S)-3-[(5-trifluoromethylthio-2,3-dihydrobenzofuran-7-yl)methyl]amino-2-phenylpiperidine hydrochloride m.p. 205°–215° C.(dec.); NMR(DMSO-$d_6$) 3.17–3.24 (2H,m, —CH2),4.55–4.62(2H,m, —CH2—), 7.42–7.53 (3H,m,Ar-H),7.61(1H,s,Ar-H),7.69–7.71(2H,m,Ar-H); Elemental Analysis ($C_{21}H_{23}F_3N_2OS.2HCl$); Calculated C:52.40 H:5.23 N:5.82; Found C:52.55 H:5.22 N:5.78

Example 31
(2S,3S)-3-[(5-(2,2,2-trifluoroethyl)thio-2,3-dihydrobenzofuran-7-yl)methyl]amino-2-phenylpiperidine hydrochloride m.p. 197°–205° C.(dec.); NMR(DMSO-$d_6$) 3.83(2H,q,J=10.26 Hz, —CH2CF3—),7.35–7.36(1H,m, Ar-H),7.42–7.53 (4H,m,Ar-H),7.71–7.74(2H,m,Ar-H); Elemental Analysis ($C_{22}H_{25}F_3N_2OS.2HCl$); Calculated C:53.34 H:5.49 N:5.65; Found C:53.35 H:5.52 N:5.57

Example 32
(2S,3S)-3-[(5-methylsulfinyl-2,3-dihydrobenzofuran-7-yl)methyl]amino-2-phenylpiperidine hydrochloride m.p. 221°–244° C.(dec.); NMR(DMSO-$d_6$) 2.69(3H,s, CH3—),7.42–7.72(7H,m,Ar-H); Elemental Analysis ($C_{21}H_{26}N_2OS.2HCl$); Calculated C:59.01 H:6.60 N:6.55; Found C:59.12 H:6.31 N:6.64

Example 33
(2S,3S)-3-[(5-isopropylsulfonyl-2,3-dihydrobenzofuran-7-yl)methyl]amino-2-phenylpiperidine hydrochloride m.p. 188°–197° C.(dec.); NMR(DMSO-$d_6$) 1.13–1.16 (6H,d,J=6.23 Hz, —CH3(i-Pr)),3,28–3.38(1H,m, —CH=(i-Pr)),7.42–7.54(3H,m,Ar-H),7.62–7.63(1H,m,Ar-H), 7.70–7.74(3H,m,Ar-H); Elemental Analysis ($C_{23}H_{30}N_2O_3S.2HCl$); Calculated C:64.54 H:7.39 N:6.84; Found C:64.51 H:7.31 N:6.94

Example 34
(2S,3S)-3-[(5-isopropylsulfonyl-2-methyl-2,3-dihydrobenzofuran-7-yl)methyl]amino-2-phenylpiperidine hydrochloride m.p. 215°–241° C.(dec.); NMR(DMSO-$d_6$) 1.14(6H,d,J=6.96 Hz, —CH3(i-Pr))),4.99–5.10(1H,m, —CH=(i-Pr)), 7.43–7.76(7H,m,Ar-H); Elemental Analysis ($C_{24}H_{32}N_2O_3S.2HCl$); Calculated C:57.48 H:6.83 N:5.59; Found C:57.71 H:6.56 N:5.38

Example 35
(2S,3S)-3-[(5-cyclopentylsulfonyl-2,3-dihydrobenzofuran-7-yl)methyl]amino-2-phenylpiperidine hydrochloride m.p. 212°–225° C.(dec.); NMR(DMSO-$d_6$) 1.50–1.91 (8H,m, —CH2—(cyclo-pentyl)),3.63–3.75(1H,m, —CH=(cyclo-pentyl)),7.42–7.54(3H,m,Ar-H), 7.65–7.77(4H,m, Ar-H); Elemental Analysis ($C_{25}H_{32}N_2O_3S.2HCl$); Calculated C:58.47 H:6.67 N:5.46; Found C:58.10 H:6.65 N:5.34

Example 36
(2S,3S)-3-[(2-methyl-5-methylaminosulfonyl-2,3-dihydrobenzofuran-7-yl)methyl]amino-2-phenylpiperidine hydrochloride

Example 37

(2S,3S)-3-[(5-methoxy-2,3-dihydrobenzofuran-7-yl) methyl]amino-2-phenylpiperidine hydrochloride m.p. 260° C.(dec.); NMR(DMSO-$d_6$) 3.68(3H,s, —OCH3),6.81–6.85(2H,m,Ar-H),7.42–7.55(3H,m,Ar-H), 7.71–7.73(2H,m,Ar-H); Elemental Analysis ($C_{21}H_{26}N_2O_2$.2HCl.0.5$H_2O$); Calculated C:60.00 H:6.95 N:6.66; Found C:60.23 H:6.98 N:6.56

Example 38

(2S,3S)-3-[(2,2-dimethyl-5-fluoro-2,3-dihydrobenzofuran-7-yl)methyl]amino-2-phenylpiperidine hydrochloride m.p. 227°–237° C.(dec.); NMR(DMSO-$d_6$) 1.375(3H,s, —CH3),1.379(3H,s, —CH3),2.98(2H,s, —CH2),6.99–7.14 (2H,m,Ar-H(F)),7.43–7.54(3H,m, Ar-H),7.71–7.73(2H,m, Ar-H); Elemental Analysis ($C_{22}H_{27}FN_2O$.2HCl); Calculated C:61.83 H:6.84 N:6.55; Found C:61.77 H:6.86 N:6.56

Example 39

(2S,3S)-3-[(5-hydroxy-2-methyl-2,3-dihydrobenzofuran-7-yl)methyl]amino-2-phenylpiperidine hydrochloride m.p. 195° C.(dec.); NMR(DMSO-$d_6$) 1.29–1.34(3H,m, —CH3),4.71–4.82(1H,m, —CH═), 6.54–6.65(2H,m,Ar-H (OH)),7.43–7.55(3H,m,Ar-H), 7.71–7.75(2H,m,Ar-H); Elemental Analysis ($C_{21}H_{26}FN_2O_2$.2HCl.$H_2O$); Calculated C:58.74 H:7.04 N:6.52; Found C:58.85 H:7.47 N:6.31

Example 40

(2S,3S)-3-[(5-fluoro-2-methyl-2,3-dihydrobenzofuran-7-yl) methyl]amino-2-phenylpiperidine hydrochloride m.p. 220°–230° C.(dec.); NMR(DMSO-$d_6$) 1.33–1.37 (3H,m, —CH3),4.83–4.93(1H,m, —CH═), 7.00–7.21(2H, m,Ar-H(F)),7.42–7.53(3H,m,Ar-H), 7.71–7.75(2H,m,Ar-H); Elemental Analysis ($C_{21}H_{25}FN_2O$.2HCl); Calculated C:61.02 H:6.58 N:6.78; Found C:60.63 H:6.48 N:6.50

Example 41

(2S,3S)-3-[(5-nitro-2,3-dihydrobenzofuran-7-yl)methyl] amino-2-phenylpiperidine hydrochloride m.p. 240°–250° C.(dec.); NMR(DMSO-$d_6$) 3.23–3.29 (2H,m, —CH2—),4.66–4.73(2H,m, —CH2—), 7.41–7.53 (3H,mAr-H),7.70–7.73(2H,m,Ar-H), 8.08(1H,d,2,2 Hz,Ar-H(—NO2)),8.26(1H,d,2,2 Hz, Ar-H(—NO2)); Elemental Analysis ($C_{20}H_{23}N_3O_3$.2HCl); Calculated C:56.34 H:5.91 N:9.86; Found C:55.91 H:5.98 N:9.53

Example 42

(2S,3S)-3-[(2-methyl-5-methylsulfonyl-2,3-dihydrobenzofuran-7-yl)methyl]amino-2-phenylpiperidine hydrochloride m.p. 225°–250° C.(dec.); NMR(DMSO-$d_6$) 1.39–1.42 (3H,m,CH3—),3,12(3H,s,CH3—),7.43–7.86(7H,m,Ar-H); Elemental Analysis ($C_{22}H_{28}N_2O_3S$.2HCl); Calculated C:55.81 H:6.39 N:5.92; Found C:55.76 H:6.23 N:5.73

Example 43

(2S,3S)-3-[2-methyl-5-methylthio-2,3-dihydrobenzofuran-7-yl)methyl]amino-2-phenylpiperidine hydrochloride m.p. 225°–240° C.; NMR(DMSO-$d_6$) 1.31–1.35(3H,m, CH3—),2,50(3H,s,CH3—),7.13–7.68(7H,m,Ar-H); Elemental Analysis $C_{22}H_{28}N_2OS$.2HCl); Calculated C:59.86 H:6.85 N:6.35; Found C:59.60 H:7.00 N:6.06

Example 44

(2S,3S)-3-[(5-dimethylaminosulfonyl-2,3-dihydrobenzofuran-7-yl)methyl]amino-2-phenylpiperidine hydrochloride m.p. 253°–275° C.(dec.); NMR(DMSO-$d_6$) 1.40–1.42 (3H,m,CH3—),2.40(3H,s,CH3—),7.43–7.75(7H,m); Elemental Analysis ($C_{22}H_{29}N_3O_3S$.2HCl); Calculated C:54.10 H:6.40 N:8.60; Found C:54.31 H:6.31 N:8.84 m.p. 236°–250° C.(dec.); NMR(DMSO-$d_6$) 2.60(6H,s, (CH3)$_2$),7.42–7.72(7H,m,Ar-H); Elemental Analysis ($C_{22}H_{29}N_3O_3S$.2HCl); Calculated C:54.10 H:6.40 N:8.60; Found C:53.85 H:6.40 N:8.44

Example 45

(2S,3S)-3-[(5-methylsulfonyl-2,3-dihydrobenzofuran-7-yl) methyl]amino-2-phenylpiperidine hydrochloride m.p. 240°–250° C.(dec.); NMR(DMSO-$d_6$) 3.12(3H,s, CH3—),7.42–7.54(3H,m,Ar-H),7.68–7.80(4H,m,Ar-H); Elemental Analysis ($C_{21}H26N_2O_3S$.2HCl); Calculated C:54.90 H:6.14 N:6.10; Found C:54.23 H:6.07 N:5.68

Example 46

(2S,3S)-3-[(5-methylthio-2,3-dihydrobenzofuran-7-yl) methyl]amino-2-phenylpiperidine hydrochloride m.p. 235°–260° C.(dec.); NMR(DMSO-$d_6$) 2.42(3H,s, CH3—),7.17(1H,s,Ar-H),7.19(1H,s,Ar-H), 7.42–7.54(3H, m,Ar-H),7.70–7.72(2H,m,Ar-H); Elemental Analysis ($C_{21}H_{26}N_2OS$.2HCl); Calculated C:59.01 H:6.60 N:6.55; Found C:59.06 H:6.60 N:6.27

Example 47

(2S,3S)-3-[(5-methyl-2,3-dihydrobenzofuran-7-yl)methyl] amino-2-phenylpiperidine hydrochloride m.p. 230°–250° C.(dec.); NMR(DMSO-$d_6$) 2.18(3H,s, CH3),6.98(1H,s,Ar-H),7.00(1H,s,Ar-H), 7.42–7.54(3H,m, Ar-H),7.72–7.75(2H,m,Ar-H); Elemental Analysis ($C_{21}H_{26}N_2O$.2HCl.$H_2O$); Calculated C:61.02 H:7.31 N:6.78; Found C:61.37 H:7.47 N:6.70

Example 48

(2S,3S)-3-[(5-chloro-2,3-dihydrobenzofuran-7-yl)methyl] amino-2-phenylpiperidine hydrochloride m.p. 260°–263° C.(dec.); NMR(DMSO-$d_6$) 3.12–3.18 (2H-,m, —HC2—),4.47–4.54(2H,m, —CH2—), 7.23–7.29 (2H,m,Ar-H(Cl)),7.42–7.54(3H,m,Ar-H), 7.69–7.71(2H,m, Ar-H); Elemental Analysis ($C_{20}H_{23}N_2OCl$.2HCl); Calculated C:57.77 H:6.06 N:6.74; Found C:57.92 H:6.14 N:6.56

Example 49

(2S,3S)-3-[(5-ethoxy-2-methyl-2,3-dihydrobenzofuran-7-yl)methyl]amino-2-phenylpiperidine hydrochloride m.p. 190°–194° C.(dec.); NMR(DMSO-$d_6$) 1.19–1.35 (6H,m, —CH3),3.89–3.97(2H,q, —CH2—), 4.75–4.85(1H, m, —CH═),6.75–6.87(2H,m,Ar-H), 7.42–7.54(3H,m,Ar-H),7.71–7.74(2H,m,Ar-H); Elemental Analysis ($C_{23}H_{30}N_2O_2$.2HCl); Calculated C:62.87 H:7.34 N:6.38; Found C:62.46 H:7.37 N:6.23

Example 50

(2S,3S)-3-[(5-cyclopentyloxy-2-methyl-2,3-dihydrobenzofuran-7-yl)methyl]amino-2-phenylpiperidine hydrochloride m.p. 182°–188° C.(dec.); NMR(DMSO-$d_6$) 1.30–1.35 (3H,m, —CH3),1.53–1.86(8H,m, —CH2—(cyclopentyl)), 4.63–4.84(2H,m, —CH═*2),6.72–6.82 (2H,m,Ar-H), 7.42–7.53(3H,m,Ar-H),7.70–7.73(2H,m,Ar-H); Elemental Analysis ($C_{26}H_{34}N_2O_2$.2HCl); Calculated C:65.13 H:7.57 N:5.84; Found C:64.83 H:7.81 N:5.52

Example 51

(2S,3S)-3-[(2,4-dimethyl-5-dimethylaminosulfonyl-2,3-dihydrobenzofuran-7-yl)methyl]amino-2-phenylpiperidine hydrochloride m.p. 221°–231° C.(dec.); NMR(DMSO-$d_6$) 1.39–1.43 (3H,m, —CH3),2,37(3H,s, —CH3),2.67(6H, s,N,N- dimethyl),4.98–5.08(1H,m, —CH═),7.43–7.52(3H,m,Ar-H),7.67–7.70(3H,m,Ar-H); Elemental Analysis ($C_{25}H_{34}N_2O_2.2HCl$); Calculated C:55.81 H:6.83 N:8.14; Found C:55.78 H:6.86 N:8.02

Example 52

(2S,3S)-3-[(2-methyl-5-(1-pyrrolidinyl)sulfonylamino-2,3-dihydrobenzofuran-7-yl)methyl]amino-2-phenylpiperidine hydrochloride m.p. 215°–224° C.(dec.); NMR(DMSO-$d_6$) 1.39–1.42 (3H,m, —CH3),1.64–1.69(4H,m, —CH2—), 4.96–5.07 (1H,m, —CH═),7.46–7.57(4H,m,Ar-H), 7.70–7.73(3H,m, Ar-H); Elemental Analysis ($C_{25}H_{33}N_3O_3S.2HCl$); Calculated C:56.81 H:6.67 N:7.95; Found C:56.41 H:6.79 N:7.68

Example 53

(2S,3S)-3-[(5-trifluoromethoxy-2,3-dihydrobenzofuran-7-yl)methyl]amino-2-phenylpiperidine hydrochloride m.p. 240°–270° C.(dec.); NMR(DMSO-$d_6$) 7.21(1H,s,Ar-H),7.26(1H,s,Ar-H),7.42–7.68(3H, m,Ar-H),7.70–7.71(2H, m,Ar-H); Elemental Analysis ($C_{21}H_{23}N_2O_2F_3.2HCl$); Calculated C:54.20 H:5.41 N:6.02; Found C:54.20 H:5.52 N:5.89

Formulation Examples

Hereinafter, Formulation Examples of the compounds of the present invention will be described.

Formulation Example 1 (Tablets)

| (1)Compound of Example 46 | 5 |
|---|---|
| (2)Lactose | 55 |
| (3)Crystalline cellulose | 18 |
| (4)Cornstarch | 18 |
| (5)Hydroxypropyl cellulose | 3 |
| (6)Magnesium stearate | 1 |
| | 100(%(w/w)) |

The above components (1) to (5) were mixed sufficiently. Water was added to the mixture, and the mixture was granulated. Then, after drying and sizing the obtained granules, the (6) was added and mixed. These mixtures were compression-molded to formulate tables each containing 100 mg of an effective component.

Formulation Example 2 (Tablets)

| (1)Compound of Example 37 | 20 |
|---|---|
| (2)Fumaric acid | 10 |
| (3)Calcium phosphate | 45 |
| (4)Lactose | 24 |
| (5)Talc | 1 |
| | 100(%(w/w)) |

On the tablets which were prepared in the same manner as described in Formulation Example 1 using the above-components (1) to (5), a coating solution comprising ethyl cellulose, polyvinyl pyrrolidone K30, talc and ethyl alcohol was spray-coated in the conventional method so as to obtain a sustained-release formulation.

Formulation Example 3 (Capsules)

| (1)Compound of Example 23 | 8 |
|---|---|
| (2)Lactose | 66 |
| (3)Corn starch | 21 |
| (4)Hydroxypropyl cellulose | 3.5 |
| (5)Light silicic anhydride | 0.5 |
| (6)Magnesium stearate | 1 |
| | 100(%(w/w)) |

After mixing the above-components (1) to (6) and making into granules in the conventional method, the granules were filled into a capsule to prepare a capsule containing 100 mg of the compound of the present invention.

Formulation Example 4 (Formulation for parenteral administration)

| (1)Compound of Example 30 | 3.0 g |
|---|---|
| (2)Soybean oil, Pharmacopoeia Japonica | 20.0 g |
| (3)Purified soybean phospholipid | 2.5 g |
| (4)Glycerine | 5.0 g |
| (5)Distilled water | 175 ml |

The above-component (1) was dissolved in the (4) and (5), previously. The oil component, in which the (2) and (3) were mixed, was added to the solution, and mixed sufficiently to prepare a formulation for parenteral administration of fat emulsion.

Formulation Example 5 (Formulation for parenteral administration)

| (1)Compound of Example 31 | 2.0 g |
|---|---|
| (2)Glycerine | 40.0 g |
| (3)Distilled water | 100 mg |

The above-component (1) was added to (2) and (3), and mixed sufficiently to prepare an aqueous formulation for parenteral administration.

Formulation Example 6 (Ointments)

| (1)Compound of Example 3 | 3.0%(w/w) |
|---|---|
| (2)Propylene glycol | 6.5%(w/w) |
| (3)Isopropyl myristate | 5.5%(w/w) |
| (4)White vaseline | 85.0%(w/w) |
| | 100%(w/w) |

An ointment was prepared in the conventional method using the above-components (1) to (4).

Formulation Example 7 (Liniments)

| (1)Compound of Example 5 | 1.0%(w/w) |
|---|---|
| (2)Ethanol | 38.0%(w/w) |
| (3)2-hydroxy-4-methoxybenzophenone | 0.5%(w/w) |
| (4)Propylene glycol | 13.0%(w/w) |
| (5)Methyl cellulose | 0.8%(w/w) |
| (6)Ethyl sebacate | 3.0%(w/w) |
| (7)Purified water | suitable amout |
| (8)Sodium hydroxide | 0.7%(w/w) |
| | 100%(w/w) |

Using the above-components (1) to (8), a liniment was prepared in the conventional method.

Formulation Example 8 (Ointments)

| (1)Compound of Example 14 | 1.0%(w/w) |
|---|---|
| (2)White vaseline | 78.0%(w/w) |
| (3)Isopropyl myristate | 12.0%(w/w) |
| (4)Spermaceti | 6.0%(w/w) |
| (5)Polyoxyethylene lauryl ether sodium phosphate | 3.0%(w/w) |
| | 100%(w/w) |

Using the above-components (1) to (5), an ointment was prepared in the conventional method.

Formulation Example 9 (Gels)

| (1)Compound of Example 17 | 3.0%(w/w) |
|---|---|
| (2)Diisopropyl adipate | 3.0%(w/w) |
| (3)Ethanol | 38.5%(w/w) |
| (4)Carboxy vinyl polymer | 2.0%(w/w) |
| (5)Purified water | suitable amount |
| (6)Hydroxypropyl cellulose | 2.0%(w/w) |
| (7)Propylene glycol | 17.0%(w/w) |
| (8)Diisopropanol amine | 2.5%(w/w) |
| | 100%(w/w) |

Using the above-components (1) to (8), a gel was prepared by the conventional method.

Formulation Example 10 (Gel creams)

| (1)Compound of Example 25 | 1.0%(w/w) |
|---|---|
| (2)Isopropyl myristate | 11.0%(w/w) |
| (3)Ethanol | 6.0%(w/w) |
| (4)Carboxy vinyl polymer | 1.5%(w/w) |
| (5)Purified water | Suitable amount |
| (6)Polyoxyethylene (55) monostearate | 1.0%(w/w) |
| (7)Coconut oil fatty acid diethanol amide | 4.0%(w/w) |
| | 100%(w/w) |

Using the above-components (1) to (7), a gel cream was prepared in the conventional method.

Formulation Example 11 (Suppositories)

| (1)Compound of Example 23 | 3.0%(w/w) |
|---|---|
| (2)Polyethylene glycol | 6.0%(w/w) |
| (3)Bleached beeswax | 10.0%(w/w) |
| (4)Sorbitan sesquioleate | 4.49%(w/w) |
| (5)Middle-chain fatty acid triglyceride | 76.5%(w/w) |
| (6)Dibutyl hydroxy toluene | 0.01%(w/w) |
| | 100%(w/w) |

Using the above-components (1) to (6), suppositories were prepared in the conventional method.

Formulation Example 12 (Poultices)

| (1)Compound of Example 24 | 3.0%(w/w) |
|---|---|
| (2)Gelatin | 9.0%(w/w) |
| (3)Aluminum silicate | 11.0%(w/w) |
| (4)Polyvinyl alcohol | 4.5%(w/w) |
| (5)Purified water | suitably amount |
| (6)Glycerine | 28.0%(w/w) |
| (7)Carboxymethyl cellulose | 3.0%(w/w) |
| | 100%(w/w) |

Using the above-components (1) to (7), a poultice was prepared in the conventional method.

Formulation Example 13 (Plasters)

| (1)Compound of Example 46 | 3.0%(w/w) |
|---|---|
| (2)Styrene-isoprene-styrene block copolymer (Califlex TR1107; Shell Chemical) | 24.0%(w/w) |
| (3)Liquid paraffin | 43.5%(w/w) |
| (4)Hydrogenated rosin ester | 29.0%(w/w) |
| | 100%(w/w) |

Using the above-components (1) to (4), a plaster was prepared by the conventional method.

Test Examples

Hereinafter, the receptor-binding test (A), the bioassay test using guinea pig ileum (B), the antagonism test on Substance P-induced air way edema (C), and the anti-emetic test (D) to cisplatin-induced emesis and toxicity test (E) of the compounds of the present invention, will be shown.

A. Receptor-Binding Test

The test was carried out based on the method described in Y. Shimohigashi, H. Matsumoto, Y. Takano et al., Biochem.Biophys.Res.Commun., 193(No.2),624–630 (1993)).

After exsanguinating guinea pigs deadly, ileum was removed and the longitudinal muscle was stripped off in ice-cold Krebes solution (127 mM NaCl, 2.2 mM KCl, 1.8 mM $CaCl_2$, 25 mM $NaHCO_3$ and 10 mM glucose). To the longitudinal muscles, 20 times of the wet weight of the buffer solution (1) (50 mM tris-HCl buffer solution containing 2 mM $MgCl_2$ and 0.1 mM phenyl methyl sulfonylfluoride, pH 7.4) was added. The mixture was homogenized under ice-cooling and centrifuged at 48,000×G for 15 minutes. After removing the supernatant, the pellets were re-suspended in the buffer solution (1) and centrifuged at 48,000×G for 15 minutes. The buffer solution (2) (50 mM tris.HCl buffer solution containing 10 mM ethylenediaminetetraacetic acid and 300 mM KCl, pH 7.4) was added to the pellets and suspended to be reacted under ice-cooling for 60 minutes. The resulted reaction materials were centrifuged at 48,000×G for 15 minutes. After suspending the pellets in the buffer solution (1) and distributing, the mixture were centrifuged at 48,000×G for 15 minutes. The pellets were stored at −80° C. until used as receptor samples.

Thus obtained receptor samples were suspended in 50 mM tris-HCl buffer solution to be used. As the buffer solution, binding buffer solution (tris.HCl buffer solution containing 0.02% bovine serum albumin, 40 $\mu$g/ml bacitracin, 4 $\mu$g/ml chymostatin, 4 $\mu$g/ml leupeptin and 3 mM $MnCl_2$, pH7.4) was used. As the reaction conditions, [$^{125}$I]SP50pM was used as a ligand, and the reaction temperature and time were at 22° C. and for 20 minutes. The results will be shown in Table 1.

B. Bioassay Test

The test was carried out based on the method described in Hiroshi Morimoto, Masako Murai, Yasue Maeda et al., J.Pharmacol.Exp.Ther., 262(No.1),398–402(1992)).

After exsanguinating guinea pigs (body weight: 500–600 g) deadly, ileum was removed and 2 cm of ileum strips were prepared. In a Tyrode's solution (10 ml, 37° C.) in which air is passed, containing 5.2 $\mu$M atropine and 4.1 $\mu$M indomethacin, the strips having 0.5 g resting tension was suspended, and contractions of muscle were recorded on a recording device (RTA-1200, manufactured by Nihon Kohden) via an isotonic transducer (TB-612T, manufactured by Nihon Kohden). Using three specimens per one group, effects of the subject drugs on the muscle contraction caused by $10^{-8}$M Substance P were determined. The muscle contraction caused by Substance P was regarded as 100%, and inhibition rates % with $10^{-7}$M drugs were determined. The results will be shown in Table 1.

Test 1

| Subject Compound (Example No.) | Binding Inhibition (%) ($10^{-8}$ M) | Contriction Inhibition (%) ($10^{-7}$ M) |
| --- | --- | --- |
| 2 | 74.8 | 47.0 |
| 3 | 96.0 | 93.2 |
| 4 | 89.7 | 60.2 |
| 5 | 91.8 | 80.5 |
| 6 | 74.8 | 50.9 |
| 7 | 54.0 | 15.0 |
| 8 | 92.0 | 85.0 |
| 9 | 36.6 | 5.5 |
| 10 | 86.2 | 61.8 |
| 11 | 85.8 | 58.2 |
| 12 | 82.2 | 43.0 |
| 13 | 84.7 | 47.4 |
| 14 | 93.5 | 92.3 |
| 15 | 88.1 | 75.2 |
| 16 | 82.5 | 78.3 |
| 17 | 94.2 | 94.6 |
| 18 | 89.9 | 81.2 |
| 19 | 48.7 | 22.1 |
| 20 | 65.0 | 38.9 |
| 21 | 53.1 | 13.4 |
| 23 | 83.2 | 80.3 |
| 24 | 50.3 | 69.5 |
| 25 | 89.2 | 85.1 |
| 26 | 56.4 | 62.1 |
| 46 | 65.3 | 72.3 |
| 53 | 53.5 | 69.3 |

As clear from the results shown in table 1, it is proved that the piperidine derivatives of the present invention have a very high antagonism on Substance P in the receptor-binding test and bioassay test.

C. Antagonism Test on Substance P-induced Airway Edema 20 mg/kg of Evans' Blue and 1 nm/kg Substance P containing 200 I.U./kg of heparin were administered intravenously to hartley male guinea pigs in order to induce airway edema. After ten minutes, the guinea pigs were exsanguinated deadly. The amounts of the dye transudated into trachea and main bronchi were determined. 1 mg/kg of the subject compounds were administered orally at thirty minutes before the induction. The results will be shown in Table 2 as the inhibition rates compared to the control group. Further, for comparison, the following compounds A and B were used.

Compound A: (2S,3S)-3-(2-methoxybenzyl)amino-2-phenylpiperidine hydrochloride

Compound B: (2S,3S)-3-(2-methoxy-5-trifluoromethoxybenzyl)amino-2-phenylpiperidine hydrochloride

TABLE 2

| Subject Compound (Example No.) | Inhibition Rate (%) |
| --- | --- |
| 23 | 89 |
| 24 | 64 |
| 25 | 90 |
| 26 | 61 |
| 46 | 72 |
| 53 | 69 |
| Compound A (10 mg/kg) | 12 |
| Compound B (1 mg/kg) | 44 |

From the results shown in Table 2, the compounds of the present invention have a very high antagonism on Substance P.

D. Anti-emetic Effect against Cisplatin-induced Emesis

The test was carried out using male ferret (approx. 1.5 kg.). Emesis was induced by intraperitoneal administration of cisplatin (10 mg/kg). 1 mg/kg of the subject compounds were administered orally just after the cisplatin administration. The results will be shown in Table 3 as the inhibition rates compared to the control group, using the number of vomits as indexes. Further, for comparisons, the following compounds A and C were used.

Compound A: (2S,3S)-3-(2-methoxybenzyl)amino-2-phenylpiperidine hydrochloride

Compound C: (2S,3S)-N-(5-isopropyl-2-methoxyphenyl)methyl-1-azabicyclo[2,2,2]octane-3-amine hydrochloride

TABLE 3

| Subject Compound (Example No.) | Inhibition Rate (%) |
| --- | --- |
| 23 | 70 |
| 25 | 73 |
| 46 | 60 |
| 53 | 65 |
| Compound A (10 mg/kg) | 19 |
| Compound C (1 mg/kg) | 10 |

From the results shown in Table 3, it is proved that the compounds of the present invention have a very high anti-emetic effect.

E. Toxicity Test 3, 10 and 30 mg/kg of the compound of Example 46 are administered to five male SD rats per one group for seven days. The compound had no influence on body weights gains, organ weights, numbers of erythrocytes nor numbers of leukocytes.

Industrial Applicability

The piperidine derivatives of the present invention have a distinguished antagonism on Substance P. The piperidine derivatives of the present invention, therefore, are expected to be used as a preventive or remedy for a variety of diseases mediated by Substance P and are useful for pharmaceutical industries.

We claim:
1. A piperidine compound selected from formula (I):

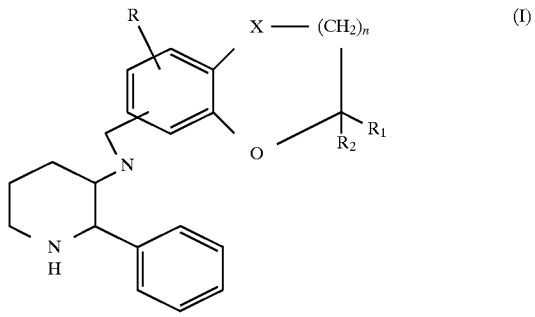

or pharmaceutically acceptable acid addition salts thereof:
wherein n represents an integer of 0 or 1; X represents $CH_2$, O or CH—$CH_3$; R represents hydrogen, halogen, lower alkyl, hydroxy, lower alkoxy, lower alkylthio, lower alkylsulfinyl, lower alkylsulfonyl, substituted aminosulfonyl or nitro; $R_1$ and $R_2$ may be the same or different and each represents hydrogen or lower alkyl.

2. A cis-piperidine compound selected from formula (Ia):

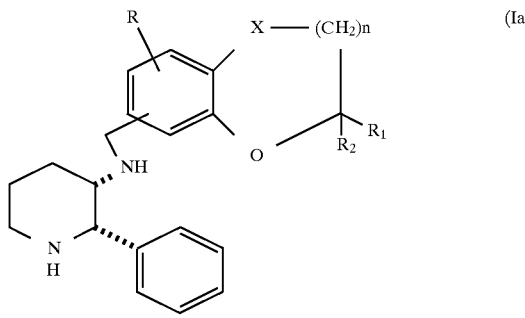

or pharmaceutically acceptable acid addition salts thereof;
wherein n represents an integer of 0 or 1; X represents $CH_2$, O or CH—$CH_3$; R represents hydrogen, halogen, lower alkyl, hydroxy, lower alkoxy, lower alkylthio, lower alkylsulfinyl, lower alkylsulfonyl, substituted aminosulfonyl or nitro; $R_1$ and $R_2$ may be the same or different and each represents hydrogen or lower alkyl.

3. A cis-piperidine compound selected from formula (Ib):

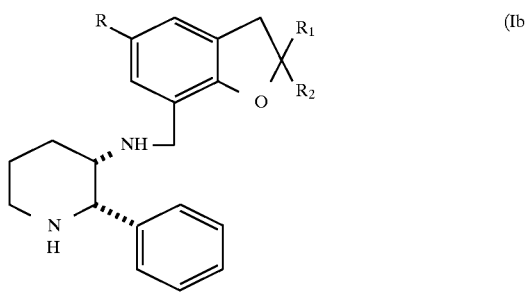

or pharmaceutically acceptable acid addition salts thereof:
wherein R represents hydrogen, halogen, lower alkyl, hydroxy, lower alkoxy, lower alkylthio, lower alkylsulfinyl, lower alkylsulfonyl, substituted aminosulfonyl or nitro; $R_1$ and $R_2$ may be the same or different and each represents hydrogen or lower alkyl.

4. A pharmaceutical composition comprising a substance P antagonistic effective amount of a piperidine compound or pharmaceutically acceptable acid addition salt thereof as claimed in claim 1 together with a pharmaceutically acceptable carrier.

5. A pharmaceutical composition comprising a substance P antagonistic effective amount of a piperidine compound or pharmaceutically acceptable acid addition salt thereof as claimed in claim 2 together with a pharmaceutically acceptable carrier.

6. A pharmaceutical composition comprising a substance P antagonistic effective amount of a piperidine compound or pharmaceutically acceptable acid addition salt thereof as claimed in claim 3 together with a pharmaceutically acceptable carrier.

7. The pharmaceutical composition of claim 4 which is for oral, parenteral, intrarectal or percutaneous administration.

8. The pharmaceutical composition of claim 5 which is for oral, parenteral, intrarectal or percutaneous administration.

9. The pharmaceutical composition of claim 6 which is for oral, parenteral, intrarectal or percutaneous administration.

10. A method of treating or preventing asthma comprising administering to a subject in need thereof, a substance P antagonistic effective amount of a piperidine compound or pharmaceutically acceptable acid addition salt thereof as claimed in claim 1.

11. A method of treating or preventing asthma comprising administering to a subject in need thereof, a substance P antagonistic effective amount of a piperidine compound or pharmaceutically acceptable acid addition salt thereof as claimed in claim 2.

12. A method of treating or preventing asthma comprising administering to a subject in need thereof, a substance P antagonistic effective amount of a piperidine compound or pharmaceutically acceptable acid addition salt thereof as claimed in claim 3.

13. A method of treating or preventing emesis comprising administering to a subject in need thereof, a substance P antagonistic effective amount of a piperidine compound or pharmaceutically acceptable acid addition salt thereof as claimed in claim 1.

14. A method of treating or preventing emesis comprising administering to a subject in need thereof, a substance P antagonistic effective amount of a piperidine compound or pharmaceutically acceptable acid addition salt thereof as claimed in claim 2.

15. A method of treating or preventing emesis comprising administering to a subject in need thereof, a substance P antagonistic effective amount of a piperidine compound or pharmaceutically acceptable acid addition salt thereof as claimed in claim 3.

* * * * *